(12) United States Patent
Paras et al.

(10) Patent No.: US 8,822,485 B2
(45) Date of Patent: Sep. 2, 2014

(54) AMINO HETEROARYL COMPOUNDS AS BETA-SECRETASE MODULATORS AND METHODS OF USE

(75) Inventors: Nick A. Paras, San Francisco, CA (US);
Yuan Cheng, Newbury Park, CA (US);
Timothy Powers, Malibu, CA (US);
James Brown, Moorpark, CA (US);
Stephen A. Hitchcock, Jupiter, FL (US);
Ted Judd, Simi Valley, CA (US);
Patricia Lopez, West Hills, CA (US);
Qiufen Xue, Newbury Park, CA (US);
Bryant Yang, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/511,360

(22) PCT Filed: Nov. 19, 2010

(86) PCT No.: PCT/US2010/057488
§ 371 (c)(1),
(2), (4) Date: Sep. 18, 2012

(87) PCT Pub. No.: WO2011/063272
PCT Pub. Date: May 26, 2011

(65) Prior Publication Data
US 2013/0018064 A1    Jan. 17, 2013

(51) Int. Cl.
*A61K 31/505* (2006.01)
(52) U.S. Cl.
USPC .......................................................... 514/269
(58) Field of Classification Search
CPC ... A61K 31/47; A61K 31/4709; C07D 215/38
USPC .......................................................... 514/269
See application file for complete search history.

(56) References Cited

U.S. PATENT DOCUMENTS

| | | | |
|---|---|---|---|
| 5,441,870 | A | 8/1995 | Seubert et al. |
| 5,712,130 | A | 1/1998 | Hajko et al. |
| 5,942,400 | A | 8/1999 | Anderson et al. |
| 2010/0041698 | A1 | 2/2010 | Amberg et al. |

FOREIGN PATENT DOCUMENTS

| | | |
|---|---|---|
| WO | 2005009969 A1 | 2/2005 |
| WO | 2007022946 A1 | 3/2007 |
| WO | 2007092854 A2 | 8/2007 |
| WO | 2009097401 A1 | 8/2009 |

OTHER PUBLICATIONS

Joachim et al., *Alz. Dis. Assoc. Dis.*, 6:7-34 (1992).
Selkoe, *Neuron*, 6:487 (1991).
Seubert et al., *Nature*, 359:325-327 (1992).
Citron, Trends in Pharmacological Sciences, 25(2):92-97 (2004).
Shnakar, G.M., *Nature Medicine* (Jun. 22, 2008) online doi 10:1038 nm 1782.
Sinha et al., *Nature*, 402:537-554 (1999) (p. 510).
Sabbagh, M. et al., *Alz. Dis. Rev.* 3:1-19 (1997).
Cole, S.L., Vasser, R., *Molecular Degeneration* 2:22, 2007.
Luo et al., *Nature Neuroscience*, 4:231-232 (2001).
*Bulletin of Experimental Biology and Medicine* 129 (6): 544-546), (2000).

*Primary Examiner* — Wu-Cheng Winston Shen
*Assistant Examiner* — Christopher R Stone
(74) *Attorney, Agent, or Firm* — G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I, wherein ring A, $B^1$, $B^2$, $B^3$, L, $R^1$, $R^4$, ring Z, m and p of Formula I are defined herein. The invention also includes use of these compounds in pharmaceutical compositions for treatment, prophylactic or therapeutic, of disorders and conditions related to the activity of beta-secretase protein. Such disorders include, for example, Alzheimer's Disease (AD), cognitive deficits, cognitive impairment, schizophrenia and other central nervous system conditions related to and/or caused by the formation and/or deposition of plaque on the brain. The invention also comprises further embodiments of Formula I, intermediates and processes useful for the preparation of compounds of Formula I.

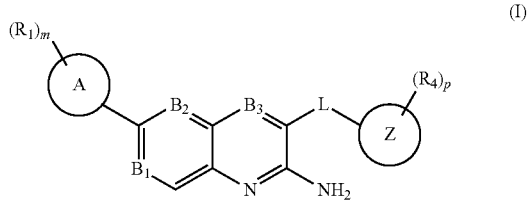

11 Claims, No Drawings

AMINO HETEROARYL COMPOUNDS AS BETA-SECRETASE MODULATORS AND METHODS OF USE

RELATED APPLICATIONS

This application is a national stage application under 35 U.S.C. §371 of International Application No. PCT/US2010/057488, having an international filing date of Nov. 19, 2010, which claims the benefit of, and priority to, U.S. Provisional Patent Application No. 61/263,743, filed on Nov. 23, 2009, which is hereby incorporated herein by reference in its entirety.

FIELD OF THE INVENTION

The invention relates generally to new compounds, pharmaceutical compositions and methods of use thereof, to treat Beta-Secretase mediated diseases and conditions, including, without limitation, Alzheimer's disease, plaque formation in the brain as well as in the peripheral central nervous system and disorders related thereto.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. $A\beta$ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shnakar, G. M., *Nature Medicine* (Jun. 22, 2008) online doi 10:1038 nm 1782.

Several aspartyl proteases are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities.

Recently dimebolin has attracted renewed interest after being shown to have positive effects on persons suffering from Alzheimer's disease. Animal studies showing potential beneficial effects on Alzheimer's disease models were shown in Russian research in 2000 (Lermontova N N, Lukoyanov N V, Serkova T P, Lukoyanova E A, Bachurin S O (June 2000). "Dimebon improves learning in animals with experimental Alzheimer's disease". *Bulletin of Experimental Biology and Medicine* 129 (6): 544-546). Preliminary results from human trials have also been promising. In an initial six-month phase II trial, results have shown that at 12 months there was significant improvement over placebo. Dimebolin appears to operate through multiple mechanisms of action, both blocking the action of neurotoxic beta amyloid proteins and inhibiting L-type calcium channels modulating the action of AMPA and NMDA glutamate receptors. To this end, inhibition of cleavage or fragmentation of beta amyloid protein via the beta secretase pathway may provide a therapeutic method for treating AD and other beta amyloid or plaque related disorders.

Several approaches have been taken to potentially treat AD and plaque-related disorders. One approach has been to attempt to reduce the formation of plaque on the brain, by inhibiting or reducing the activity of BACE. For example, each of the following PCT publications: WO 03/045913, WO 04/043916, WO 03/002122, WO 03/006021, WO 03/002518, WO 04/024081, WO 03/040096, WO 04/050619, WO 04/080376, WO 04/099376, WO 05/004802, WO 04/080459, WO 04/062625, WO 04/042910, WO 05/004803, WO 05/005374, WO 03/106405, WO 03/062209, WO 03/030886, WO 02/002505, WO 01/070671, WO 03/057721, WO 03/006013, WO 03/037325, WO 04/094384, WO 04/094413, WO 03/006423, WO 03/050073, WO 03/029169 and WO 04/000821, describe inhibitors of BACE, potentially useful for treating AD and other beta-secretase mediated disorders. Despite these efforts, there is always a need to find new compounds which may effectively treat such plaque-related conditions and disorders, such as AD.

BRIEF DESCRIPTION OF THE INVENTION

The present invention provides a new class of compounds useful for the modulation of beta secretase activity. To that end, the compounds of the invention are useful for the regulation or reduction of the formation of A-beta peptide and, consequently, the regulation and/or reduction of beta amyloid plaque formation on the brain. Accordingly, the compounds are useful for the treatment of Alzheimer's disease and other beta secretase and/or plaque mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, solvates, pharmaceutically acceptable salts, derivatives or prodrugs thereof, are generally defined by Formula I

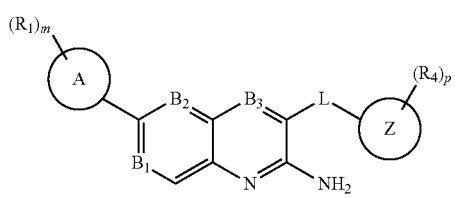

wherein ring A, $B^1$, $B^2$, $B^3$, L, $R^1$, $R^4$, ring Z, m and p of Formula I are defined herein below. The invention also provides compounds of sub-formulas of Formula I, as well as procedures for making compounds of Formula I and intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are generally defined by

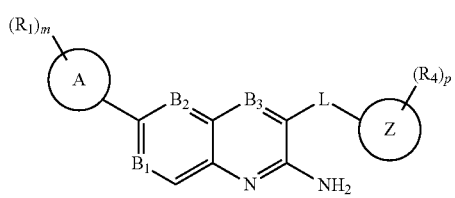

or a stereoisomer, tautomer or pharmaceutically acceptable salt thereof, wherein A is a 5- or 6-membered aryl or heteraryl ring;

each of $B^1$, $B^2$ and $B^3$, independently, is N, —CF, —$CCH_3$ or CH;

L is —$CR^2R^2$—$(CR^3R^3)_o$—, —$CR^2R^2$—O—, —C≡C—, $C_{3-8}$cycloalkyl, tetrahydrofuranyl or tetrahydropyranyl, wherein the $C_{3-8}$cycloalkyl, tetrahydrofuranyl and tetrahydropyranyl are optionally substituted with 1-4 substituents of $R^4$, and wherein each $R^2$, independently, is H, $C_{1-3}$alkyl or halo; and each $R^3$, independently, is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl and o is 1 or 2;

each $R^1$ independently, is F, Cl, Br, $CF_3$, $OCF_3$, $C_{1-6}$-alkyl, CN, OH, —$OC_{1-6}$-alkyl, —$S(O)_nC_{1-6}$-alkyl, —$NH_2$, CN, —$NHC_{1-6}$-alkyl, —$C(O)C_{1-6}$-alkyl, —C(O)-cycloalkyl or —$C(O)NR^aR^b$ wherein $R^a$ is H or $C_{1-6}$alkyl and $R^b$ is $R^4$;

alternatively, $R^a$ and $R^b$ taken together with the nitrogen atom to which they are attached form a 4-7 membered monocyclic heterocycle, wherein the carbocycle of the —C(O)-carbocycle and monocyclic heterocycle are optionally substituted with 1-3 substituents of $R^4$;

each $R^4$, independently, is halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxy, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

Z is a 6-membered monocyclic or 10-membered bicyclic aryl ring or 5- or 6-membered monocyclic or 9-10-membered bicyclic heteraryl ring;

m is 0, 1, 2, 3, 4 or 5;

n is 0, 1 or 2; and p is 0, 1, 2, 3, 4 or 5.

In another embodiment, the compounds of Formula I includes compounds wherein ring A is an optionally substituted 5- or 6-membered aryl or heteroaryl or a 3- to 8-membered cycloalkyl or heterocyclyl, in conjunction with any of the above or below embodiments.

In another embodiment, the compounds of Formula I include compounds wherein ring A is an optionally substituted 5- or 6-membered aryl or heteroaryl, in conjunction with any of the above or below embodiments.

In another embodiment, the compounds of Formula I include compounds wherein ring A is an optionally substituted 5-membered heteroaryl, in conjunction with any of the above or below embodiments.

In another embodiment, the compounds of Formula I include compounds wherein ring A is an optionally substituted 6-membered heteroaryl, in conjunction with any of the above or below embodiments.

In another embodiment, the compounds of Formula I include compounds wherein ring A is an optionally substituted 6-membered aryl, in conjunction with any of the above or below embodiments.

In another embodiment, the compounds of Formula I include compounds wherein ring A is an optionally substituted phenyl, pyridine, pyrimidine, triazine, pyrazine, pyridazine, imidazole, pyrazole, thiazole, oxazole, isoxazole, isothiazole, pyrrole, furan, thiophene, cyclopropane, cyclobutane, cyclopentane, cyclohexane, morpholine, piperidine or piperazine ring, in conjunction with any of the above or below embodiments.

In another embodiment, the compounds of Formula I include compounds wherein ring A is an optionally substituted phenyl, pyridine, pyrimidine, triazine, cyclopropane or thiophene, in conjunction with any of the above or below embodiments.

In another embodiment, the compounds of Formula I include compounds wherein ring A is a phenyl, pyridine, pyrimidine, triazine or thiophene, in conjunction with any of the above or below embodiments.

In another embodiment, the compounds of Formula I include compounds wherein ring A is a phenyl, 2-pyridyl, 3-pyridyl or 4-pyridyl ring, in conjunction with any of the above or below embodiments.

In another embodiment, Formulas I and I-B include compounds wherein $B^1$ is $CR^2$, in conjunction with any of the above or below embodiments.

In another embodiment, Formulas I and I-B include compounds wherein $B^1$ is N, in conjunction with any of the above or below embodiments.

In another embodiment, the compounds of Formula I include compounds wherein $B^2$ is $CR^2$, in conjunction with any of the above or below embodiments.

In another embodiment, the compounds of Formula I include compounds wherein $B^2$ is N, in conjunction with any of the above or below embodiments.

In another embodiment, the compounds of Formula I include compounds wherein $B^2$ is CH, in conjunction with any of the above or below embodiments.

In another embodiment, Formulas I and I-B include compounds wherein $B^1$ is CH, in conjunction with any of the above or below embodiments.

In another embodiment, Formulas I and I-B include compounds wherein $B^3$ is N, in conjunction with any of the above or below embodiments.

In another embodiment, Formulas I and I-B include compounds wherein $B^3$ is CH, in conjunction with any of the above or below embodiments.

In another embodiment, the compounds of Formula I include compounds wherein $B^1$ is $CR^2$ and $B^2$ is $CR^2$, in conjunction with any of the above or below embodiments.

In another embodiment, the compounds of Formula I include compounds wherein $B^1$ is $CR^2$ and $B^2$ is CH, in conjunction with any of the above or below embodiments.

In another embodiment, the compounds of Formula I include compounds wherein $B^1$ is N and $B^2$ is $CR^2$, in conjunction with any of the above or below embodiments.

In another embodiment, the compounds of Formula I include compounds wherein $B^1$ is N and each of $B^2$ and $B^3$, independently, is $CR^2$, in conjunction with any of the above or below embodiments.

In another embodiment, the compounds of Formula I include compounds wherein $B^3$ is N and each of $B^1$ and $B^2$, independently, is $CR^2$, in conjunction with any of the above or below embodiments.

In another embodiment, the compounds of Formula I include compounds wherein $B^1$ is $CR^2$ and $B^2$ is N, in conjunction with any of the above or below embodiments.

In another embodiment, Formulas I and I-B include compounds wherein one of $B^1$ and $B^3$ is N and the other of $B^1$ and $B^3$ is $CR^2$, in conjunction with any of the above or below embodiments.

In another embodiment, the compounds of Formula I include compounds wherein $B^1$ is N and $B^2$ is N, in conjunction with any of the above or below embodiments.

In one embodiment of the invention, the compounds, including stereoisomers, tautomers, solvates, pharmaceutically acceptable salts, derivatives or prodrugs thereof, are generally defined by Formula I-A

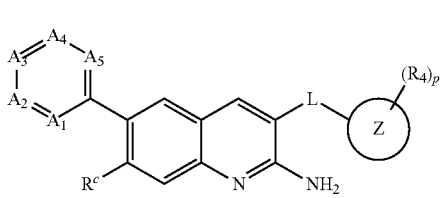

I-A

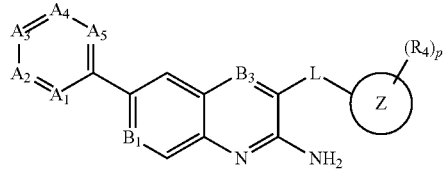

I-B or a stereoisomer or pharmaceutically acceptable salt thereof, wherein $A^1$ is $CR^1$ or N;

$A^2$ is $CR^1$ or N;

$A^3$ is $CR^1$ or N;

$A^4$ is $CR^1$ or N;

$A^5$ is $CR^1$ or N, provided no more than two of $A^1, A^2, A^3, A^4$ and $A^5$ is N;

each of $R^1$ independently, is H, F, Cl, Br, $CF_3$, $OCF_3$, $C_{1-6}$-alkyl, CN, OH, —$OC_{1-6}$-alkyl, —$S(O)_6C_{1-6}$-alkyl, —$NH_2$, CN, —$NHC_{1-6}$-alkyl or —$C(O)C_{1-6}$-alkyl;

$R^c$ is H, $C_{1-3}$alkyl or halo;

L is —$CR^2R^2$—$(CR^3R^3)$—, —$CR^2R^2$—O—, —$CR^2$=$CR^3$—, —C≡C—, $C_{3-8}$cycloalkyl, tetrahydrofuranyl or tetrahydropyranyl, wherein the $C_{3-8}$cycloalkyl, tetrahydrofuranyl and tetrahydropyranyl are optionally substituted with 1-4 substituents of $R^4$, and wherein each $R^2$, independently, is H, $C_{1-3}$alkyl or F; and each $R^3$, independently, is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl;

each $R^4$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

Z is a ring selected from phenyl, pyridyl, pyrimidyl, thienyl, furanyl, pyrrolyl, pyrazolyl, imidazolyl, triazolyl, tetrazolyl, thiazolyl, oxazolyl, isothiazolyl, isoxazolyl, diazolyl, thiodiazolyl, oxadiazolyl, pyrazinyl, pyridazinyl and indolyl; and p is 0, 1, 2, 3 or 4.

In one embodiment of the invention, the compounds, including stereoisomers, tautomers, solvates, pharmaceutically acceptable salts thereof, are generally defined by Formula I-B wherein $A^1$ is $CR^1$ or N;

$A^2$ is $CR^1$ or N;

$A^3$ is $CR^1$ or N;

$A^4$ is $CR^1$ or N;

$A^5$ is $CR^1$ or N, provided no more than two of $A^1, A^2, A^3, A^4$ and $A^5$ is N;

each of $B^1$ and $B^3$, independently, is N, —CF, —$CCH_3$ or CH;

L is —$CR^2R^2$—$(CR^3R^3)$—, —$CR^2R^2$—O—, —$CR^2$=$CR^3$—, —C≡C—, $C_{3-8}$cycloalkyl, tetrahydrofuranyl or tetrahydropyranyl, wherein the $C_{3-8}$cycloalkyl, tetrahydrofuranyl and tetrahydropyranyl are optionally substituted with 1-4 substituents of $R^4$, and wherein each $R^2$, independently, is H, $C_{1-3}$alkyl or F; and each $R^3$, independently, is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl;

each of $R^1$ independently, is H, F, Cl, Br, $CF_3$, $OCF_3$, CN, OH, —$OC_{1-6}$-alkyl, —$S(O)_oC_{1-6}$-alkyl, —$NH_2$, CN, —$NHC_{1-6}$-alkyl, —$C(O)C_{1-6}$-alkyl, —$C(O)C_{1-6}$-alkyl-$R^4$ or —$C(O)$—$R^4$;

each $R^4$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

Z is a ring selected from phenyl, pyridyl, pyrimidyl, thienyl, furanyl, pyrrolyl, pyrazolyl, imidazolyl, triazolyl, tetrazolyl, thiazolyl, oxazolyl, isothiazolyl, isoxazolyl, diazolyl, thiodiazolyl, oxadiazolyl, pyrazinyl, pyridazinyl and indolyl; and p is 0, 1, 2, 3 or 4.

In another embodiment, the compounds of Formula I-A and I-B include compounds wherein $A^1$ is $CR^1$, in conjunction with any of the above or below embodiments.

In another embodiment, the compounds of Formula I-A and I-B include compounds wherein $A^1$ is N, in conjunction with any of the above or below embodiments.

In another embodiment, the compounds of Formula I-A and I-B include compounds wherein $A^2$ is $CR^1$, in conjunction with any of the above or below embodiments.

In another embodiment, the compounds of Formula I-A includes compounds wherein $A^2$ is N, in conjunction with any of the above or below embodiments.

In another embodiment, the compounds of Formula I-A and I-B include compounds wherein $A^3$ is $CR^1$, in conjunction with any of the above or below embodiments.

In another embodiment, the compounds of Formula I-A and I-B include compounds wherein $A^3$ is N, in conjunction with any of the above or below embodiments.

In another embodiment, the compounds of Formula I-A and I-B include compounds wherein $A^4$ is $CR^1$, in conjunction with any of the above or below embodiments.

In another embodiment, the compounds of Formula I-A and I-B include compounds wherein $A^4$ is N, in conjunction with any of the above or below embodiments.

In another embodiment, the compounds of Formula I-A and I-B include compounds wherein $A^5$ is $CR^1$, in conjunction with any of the above or below embodiments.

In another embodiment, the compounds of Formula I-A and I-B include compounds wherein $A^5$ is N, in conjunction with any of the above or below embodiments.

In another embodiment, the compounds of Formula I-A and I-B include compounds wherein one of $A^1$, $A^2$, $A^3$, $A^4$ and $A^5$ is N and the other four of $A^1$, $A^2$, $A^3$, $A^4$ and $A^5$ is $CR^1$, in conjunction with any of the above or below embodiments.

In another embodiment, the compounds of Formula I-A and I-B include compounds wherein one of $A^1$ and $A^2$ is N and the other of $A^1$ and $A^2$ is $CR^1$, $A^3$ is $CR^1$, $A^4$ is $CR^1$ and $A^5$ is $CR^1$, in conjunction with any of the above or below embodiments.

In another embodiment, the compounds of Formula I-A and I-B include compounds wherein each of $A^1$, $A^2$, $A^3$, $A^4$ and $A^5$ is $CR^1$ as defined in Formula I, in conjunction with any of the above or below embodiments.

In another embodiment, the compounds of Formula I-A and I-B include compounds wherein each of $A^1$, $A^2$, $A^3$, $A^4$ and $A^5$, independently, is $CR^1$ wherein each $R^1$, independently, is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, Formulas I, I-A and I-B include compounds wherein
L is —$CR^2R^2$—$(CR^3R^3)_o$—, —$CR^2R^2$—O—, —$CR^2$=$CR^3$—, —C≡C—, $C_{3-8}$cycloalkyl, tetrahydrofuranyl or tetrahydropyranyl, wherein the $C_{3-8}$cycloalkyl, tetrahydrofuranyl and tetrahydropyranyl are optionally substituted with 1-4 substituents of $R^4$, and wherein each $R^2$, independently, is H, $C_{1-3}$alkyl or halo; and
each $R^3$, independently, is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl and o is 1 or 2, in conjunction with any of the above or below embodiments.

In another embodiment, Formulas I, I-A and I-B include compounds wherein
L is —$CR^2R^2$—$(CR^3R^3)$—, —$CR^2R^2$—O—, —$CR^2$=$CR^3$—, —C≡C—, $C_{3-8}$cycloalkyl, tetrahydrofuranyl or tetrahydropyranyl, wherein the $C_{3-8}$cycloalkyl, tetrahydrofuranyl and tetrahydropyranyl are optionally substituted with 1-4 substituents of $R^4$, and wherein each $R^2$, independently, is H, $C_{1-3}$alkyl or F; and
each $R^3$, independently, is H, $C_{1-6}$alkyl, $C_{3-6}$cycloalkyl, —OH, —$OC_{1-4}$alkyl, halo,
haloalkyl, CN, —$NH_2$ or —$NHC_{1-6}$alkyl, in conjunction with any of the above or below embodiments.

In another embodiment, Formulas I, I-A and I-B include compounds wherein L is —$CH_2$—$CH(C_{1-6}$alkyl)-, —$CH_2$—O—, —CH=CH—, $C_{3-8}$cycloalkyl, tetrahydrofuranyl or tetrahydropyranyl, wherein the $C_{3-8}$cycloalkyl, tetrahydrofuranyl and tetrahydropyranyl are optionally substituted with 1-4 substituents of $R^4$, in conjunction with any of the above or below embodiments.

In another embodiment, Formulas I, I-A and I-B include compounds wherein L is —$CH_2$—$CH(C_{1-6}$alkyl)-, —$CH_2$—O—, —CH=CH—, cyclopropyl, cyclobutyl, cyclopentyl, cyclohexyl, tetrahydropyranyl or tetrahydrofuranyl, wherein the cyclopropyl, cyclobutyl, cyclopentyl, cyclohexyl, tetrahydropyranyl and tetrahydrofuranyl are optionally substituted with 1-4 substituents of $R^4$, in conjunction with any of the above or below embodiments.

In another embodiment, Formulas I, I-A and I-B include compounds wherein L is —$CR^2R^2$—$(CR^3R^3)_o$— wherein o is 1 or 2, and each $R^3$ independently is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl, in conjunction with any of the above or below embodiments.

In another embodiment, Formulas I, I-A and I-B include compounds wherein L is —$CR^3R^3$—$CR^3R^3$—$CH_2$— wherein each $R^3$ independently is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl, in conjunction with any of the above or below embodiments.

In another embodiment, Formulas I, I-A and I-B include compounds wherein L is —$CHR^3$—$CHR^3$— wherein each $R^3$ independently is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl, in conjunction with any of the above or below embodiments.

In another embodiment, Formulas I, I-A and I-B include compounds wherein L is —$CH_2$—$CHR^3$— wherein $R^3$ is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl, in conjunction with any of the above or below embodiments.

In another embodiment, Formulas I, I-A and I-B include compounds wherein L is —$CH_2$—$CHR^3$— wherein $R^3$ is methyl, ethyl, propyl, cyclopropyl, cyclobutyl, cyclopentyl, cyclohexyl, —OH, —$OCH_3$, F, Cl, Br, —$OCF_3$, CN, —$NH_2$ or —$NHC_{1-3}$alkyl, in conjunction with any of the above or below embodiments.

In another embodiment, Formulas I, I-A and include compounds wherein L is —$CH_2$—$CHR^3$— wherein $R^3$ is methyl, ethyl, propyl or F, in conjunction with any of the above or below embodiments.

In another embodiment, Formulas I, I-A and I-B include compounds wherein L is —$CH_2$—$CHR^3$— wherein $R^3$ is methyl, in conjunction with any of the above or below embodiments.

In another embodiment, Formulas I, I-A and I-B include compounds wherein L is —$(CR^3R^3)_o$— wherein o is 2 or 3 and each $R^3$ independently is H, methyl, ethyl, propyl, cyclopropyl, cyclobutyl, cyclopentyl, cyclohexyl, —OH, —$OCH_3$, F, Cl, Br, —$OCF_3$, CN, —$NH_2$ or —$NHC_{1-3}$alkyl, in conjunction with any of the above or below embodiments.

In another embodiment, Formulas I, I-A and I-B include compounds wherein each $R^1$ independently, is F, Cl, Br, $CF_3$, $OCF_3$, CN, OH, —$OC_{1-6}$-alkyl, —$S(O)_6C_{1-6}$-alkyl, —$NH_2$, CN, —C(O)—$C_{1-6}$cycloalkyl or —C(O)$NR^aR^b$ wherein $R^a$ is H or $C_{1-6}$alkyl and $R^b$ is $R^4$;

alternatively, $R^a$ and $R^b$ taken together with the nitrogen atom to which they are attached form a 4-7 membered monocyclic heterocycle, wherein the $C_{1-6}$cycloalkyl of the —C(O) $C_{1-6}$cycloalkyl and monocyclic heterocycle are optionally substituted with 1-3 substituents of $R^4$, in conjunction with any of the above or below embodiments.

In another embodiment, Formulas I, I-A and I-B include compounds wherein each $R^1$ independently, is F, Cl, $CF_3$, $OCF_3$, methyl, ethyl, CN, OH, —$OCH_3$, —$OCF_3$, —$NH_2$, $NHCH_3$, $C(O)C_{1-6}$cycloalkyl or —$C(O)CH_3$, in conjunction with any of the above or below embodiments.

In another embodiment, Formulas I, I-A and I-B include compounds wherein each of $R^1$ is F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, Formulas I, I-A and I-B include compounds wherein each $R^1$ independently, is F, Cl, Br, $CF_3$, $OCF_3$, CN, OH, —$OC_{1-6}$-alkyl, —$S(O)_nC_{1-6}$-alkyl, —$NH_2$, CN, —$C(O)C_{1-6}$-alkyl, —$C(O)C_{1-6}$cycloalkyl, —$C(O)$—tetrahydropyrrole, in conjunction with any of the above or below embodiments.

In another embodiment, Formulas I and I-A include compounds wherein each $R^2$, independently, is H, $C_{1-3}$alkyl or halo, in conjunction with any of the above or below embodiments.

In another embodiment, Formulas I, I-A and I-B include compounds wherein each $R^2$, independently, is H, $CH_3$, $CH_2CH_3$, F or Cl, in conjunction with any of the above or below embodiments.

In another embodiment, Formulas I, I-A and I-B include compounds wherein each $R^2$, independently, is H, in conjunction with any of the above or below embodiments.

In another embodiment, Formulas I, I-A and I-B include compounds wherein each $R^3$ independently is H, $C_1$ alkyl, $C_{3-6}$cycloalkyl, —OH, —$OC_{1-4}$alkyl, halo, haloalkyl, CN, —$NH_2$ or —$NHC_{1-6}$alkyl, in conjunction with any of the above or below embodiments.

In another embodiment, Formulas I, I-A and I-B include compounds wherein each $R^3$ independently is H or methyl, in conjunction with any of the above or below embodiments.

In another embodiment, Formulas I, I-A and I-B include compounds wherein $R^4$ is a fully saturated or partially or fully unsaturated 5- or 6-membered monocyclic or bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, cycloalkyl, $C_{4-8}$-cycloalkenyl and ring are optionally substituted, independently, with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In another embodiment, Formulas I, I-A and I-B include compounds wherein $R^4$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In another embodiment, Formulas I, I-A and I-B include compounds wherein $R^4$ is halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In another embodiment, Formulas I, I-A and I-B include compounds wherein $R^4$ is $C_{1-4}$alkyl substituted with 1-3 substituents of F, Cl, Br, I, $CF_3$, $C_2F_5$ and haloalkoxyl, or $R^4$ is F, Cl, Br, I, $CF_3$, $C_2F_5$, haloalkoxyl, CN, OH, $OC_{1-6}$-alkyl, $SC_{1-6}$-alkyl, $SC_{1-6}$-alkyl, $S(O)_oC_{1-6}$-alkyl, cycloalkyl, aryl, heteroaryl or heterocyclyl wherein the cycloalkyl, aryl, heteroaryl or heterocyclyl is optionally substituted independently with 1-5 substituents of F, Cl, Br, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-4}$-dialkylamino- or $C_{1-4}$-thioalkoxyl, in conjunction with any of the above or below embodiments.

In another embodiment, Formulas I, I-A and I-B include compounds wherein $R^4$ is F, Cl, Br, I, $CF_3$, $C_2F_5$, haloalkoxyl, $C_{1-6}$-alkyl, CN, OH, $OC_{1-6}$-alkyl, $SC_{1-6}$-alkyl, $SC_{1-6}$-alkyl, $S(O)_oC_{1-6}$-alkyl wherein o is 0, 1 or 2, $NHC_{1-6}$-alkyl or $C(O)C_{1-6}$-alkyl, in conjunction with any of the above or below embodiments.

In another embodiment, the invention provides the compound of Formula I, I-A or I-B, or a stereoisomer or pharmaceutically acceptable salt thereof, selected from 3-(2-(6-cyclopentylpyrimidin-4-yl)cyclopentyl)-6-o-tolylquinolin-2-amine;

3-(2-(5-cyclohexenylpyridin-3-yl)vinyl)-6-o-tolylquinolin-2-amine;

3-(2-(5-cyclohexylpyridin-3-yl)ethyl)-6-o-tolylquinolin-2-amine;

3-(2-(5-isobutylpyridin-3-yl)vinyl)-6-o-tolylquinolin-2-amine;

3-(2-(5-ethylpyridin-3-yl)ethyl)-6-o-tolylquinolin-2-amine;

3-(2-(5-ethylpyridin-3-yl)ethyl)-6-o-tolylquinolin-2-amine;

of 3-(3-(6-neopentylpyrimidin-4-yl)tetrahydro-2H-pyran-2-yl)-6-o-tolylquinolin-2-amine;

3-(2-(6-tert-butylpyrimidin-4-yl)ethyl)-6-o-tolylquinolin-2-amine;

3-(2-(6-neopentylpyrimidin-4-yl)propyl)-6-o-tolylquinolin-2-amine;

3-(2-(6-ethylpyrimidin-4-yl)propyl)-6-o-tolylquinolin-2-amine;

6-o-tolyl-3-((6-(trifluoromethyl)pyrimidin-4-yloxy)methyl)quinolin-2-amine;

3-(2-(6-cyclopentylpyrimidin-4-yl)propyl)-6-o-tolylquinolin-2-amine;

6-o-tolyl-3-((6-ethylpyrimidin-4-yloxy)methyl)quinolin-2-amine;

6-(3-methylpyridin-2-yl)-3-(2-(6-neopentylpyrimidin-4-yl)propyl)quinolin-2-amine;

3-(2-(6-tert-burylpyrimidin-4-yl)ethyl)-6-(3-methylpyridin-2-yl)quinolin-2-amine;
3-(2-(1H-indol-2-yl)ethyl)-6-o-tolylquinolin-2-amine;
3-(2-(5-isobutylpyridin-3-yl)ethyl)-6-o-tolylquinolin-2-amine;
3-(2-(1-benzyl-1H-pyrazol-4-yl)ethyl)-6-o-tolylquinolin-2-amine;
6-(3-methylpyridin-2-yl)-3-(2-(6-(tetrahydro-2H-pyran-4-yl)pyrimidin-4-yl)ethyl)quinolin-2-amine;
3-(2-(5-neopentylpyridin-3-yl)ethyl)-6-o-tolylquinolin-2-amine;
3-(2-(5-(3,3-dimethylbutyl)pyridin-3-yl)ethyl)-6-o-tolylquinolin-2-amine;
6-o-tolyl-3-(3-(trifluoromethyl)phenethyl)quinolin-2-amine;
3-(2-(1-cyclohexyl-1H-pyrazol-4-yl)vinyl)-6-o-tolylquinolin-2-amine;
3-(2-(1-cyclohexyl-1H-pyrazol-4-yl)ethyl)-6-o-tolylquinolin-2-amine;
3-(2-(5-(tetrahydro-2H-pyran-2-yl)pyridin-3-yl)propyl)-6-o-tolylquinolin-2-amine;
3-(2-(5-cyclohexylpyridin-3-yl)propyl)-6-o-tolylquinolin-2-amine;
3-(2-(oxazol-5-yl)ethyl)-6-o-tolylquinolin-2-amine;
3-(2-(pyridin-2-yl)ethyl)-6-o-tolylquinolin-2-amine;
3-(2-(5-cyclopentylpyridin-3-yl)propyl)-6-o-tolylquinolin-2-amine;
3-(2-(5-(tetrahydro-2H-pyran-2-yl)pyridin-3-yl)ethyl)-6-o-tolylquinolin-2-amine;
(±)-(2-(2-amino-3-(2-(pyrimidin-5-yl)ethyl)quinolin-6-yl)-3-methylphenyl)(2-methylpyrrolidin-1-yl)methanone;
(2-(2-amino-3-(2-(pyrimidin-5-yl)ethyl)quinolin-6-yl)-3-methylphenyl)(pyrrolidin-1-yl)methanone; and
(2-(2-amino-3-((6-(trifluoromethyl)pyrimidin-4-yloxy)methyl)quinolin-6-yl)-3-methylphenyl)(pyrrolidin-1-yl)methanone.

In another embodiment, the invention provides each of the Exemplary compounds, and stereoisomers, tautomers, solvates, pharmaceutically acceptable salts, derivatives or prodrugs thereof, and related intermediates, described herein.

In another embodiment, the invention provides the exemplified compounds described herein, and stereoisomers and pharmaceutically acceptable salt forms of each thereof.

DEFINITIONS

The following definitions should assist in understanding the invention described herein.

The term "comprising" is meant to be open-ended, i.e., all encompassing, all inclusive and non-limiting. It may be used herein synonymously with "having" or "including." "Comprising" is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$, or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl(propargyl), butynyl, and the like.

The term "$C_{\alpha-\beta}$alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$alkyl. Examples of such "alkenyl" radicals include —NH—CH$_2$CH═CH$_2$, —S—CH$_2$CH$_2$CH═CHCH$_3$ and the like. Similar examples exist for such "alkynyl" radicals, as appreciated by those skilled in the art.

The term "$_{\alpha-\beta}$alkoxyl" when used alone or in combination, embraces linear or branched oxygen-containing alkyl radicals each having a to number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted at two carbons with —O—CH$_2$—O— or —O—CH$_2$—CH$_2$—O— form an aryl benzodioxolyl substituent.

The term "cycloalkyl", also referred to herein as "carbocyclic" or "carbocyclyl", when used alone or in combination, means a partially or fully saturated ring moiety formed of carbon atoms and comprising one ("monocyclic"), two ("bicyclic") or even three ("tricyclic") rings wherein such rings may be attached together in a fused manner. Examples of saturated cycloalkyl radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine (F), chlorine (Cl), bromine (Br) or iodine (I) atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl ($CF_3$), chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The phrase "a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S" as used herein is intended to encompass all monocyclic and bicyclic rings as small as three atoms to as large as 12 atoms in size, including both carbocyclic rings and heterocyclic, aromatic and non-aromatic rings. The non-aromatic rings may be partially or fully saturated in nature.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)NH$_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, (CH$_3$S—).

The term "Formula I" includes any sub formulas, such as Formulas I-A and Formulas I-B.

The term "pharmaceutically-acceptable" when used with reference to a compound of Formulas I, I-A and I-B is intended to refer to a form of the compound that is safe for administration. For example, a salt form, a solvate, a hydrate, a prodrug or derivative form of a compound of Formulas I, I-A and I-B, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I, I-A and I-B are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I, I-A and I-B may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I, I-A and I-B include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I, I-A and I-B.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability of the derivative to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formulas I, I-A and I-B. A "pharmaceutically-acceptable prodrug" as used herein, denotes a prodrug which is pharmaceutically acceptable. Pharmaceutically acceptable modifications to the compounds of Formula I, I-A and I-B are readily appreciated by those of ordinary skill in the art.

The compound(s) of Formulas I, I-A and I-B may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, I-A and I-B. The compounds of Formulas I, I-A and I-B can be synthesized according to the procedures described in the following Schemes 1, 2, 3a, 3b, 4 and 5, wherein the substituents are as defined for Formulas I, I-A and I-B above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DIC—1,3-diisopropylcarbodiimide
DIEA, DIPEA—N,N-diisopropylethylamine
DME—dimethoxyethane
DMF—N,N-dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
NMP—N-methylpyrrolidine
$P(t-bu)_3$—tri(tert-butyl)phosphine
PBS—phospate buffered saline
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium flouride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light Scheme I

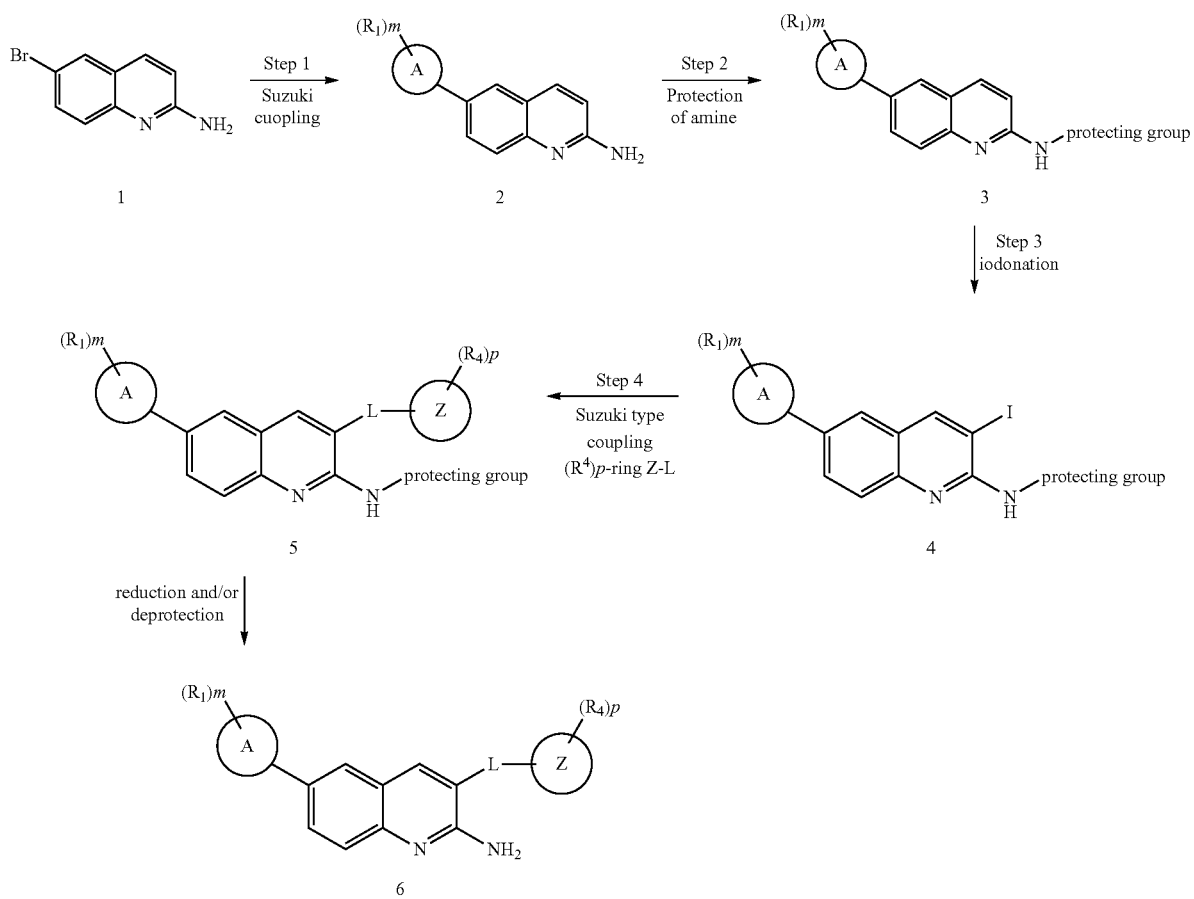

Compounds 6 of formulas I, I-A and I-B may be prepared by the method illustrated in scheme I and described step-by-step below.

6-Bromo-2-amino quinoline 1 (may be purchased or made separated by known published methods, as discussed hereinbelow) may be reacted with a desirably substituted aromatic or heteroaromatic boronic acid A, to afford the desired product 2 of step 1. The amino group of the step 1 adduct 2 may be protected suitably to proceed to prepare protected compound 3. See example 1 for a representative protecting group. The protected adduct 3 may then be iodinated at the 3-position using conventional methods to afford intermediate 4. See example 1 for a representative method. The iodinated product 4 can be treated with desired L-Z-$(R^4)_p$ groups, which can be made separately by known methods, using conventional methods, such as adopting palladium catalyzed reactions, to build the linkage between the L group and the quinoline core ring and produce compound 5. Compound 5 can be deprotected or otherwise functionalized as desired, followed by deprotection, to provide compounds 6.

The boronic acid, and/or ester, intermediates may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be commercially purchased or internally prepared as needed.

Step 1 involves a boronic acid coupling reaction, similar to classic Suzuki reactions using a borane reagent and a suitable aromatic bromide, such as the Br-quinoline 1 (Br is a suitable halogen leaving group "LG"). As appreciated to one of ordinary skill in the art, Suzuki and Suzuki-like reactions also utilize a palladium catalyst. Suitable palladium catalysts include, without limitation, $Pd(PPh_3)_4$, $Pd(OAc)_2$ or $Pd(dppf)Cl_2$. Where LG is a halide, the halide may be an iodide, a bromide or even a chloride. Chloro-pyridyl rings (where $A^1$=N) undergo Suzuki reactions in the presence of $Pd(OAc)_2$. Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Alternatively, the reaction may simply require solvent and heat depending upon the particular bromide 3 and/or boronic acid or ester, as appreciated by those skilled in the art. Other methods of installing the boronate on a desired aromatic ring are known. For example metal coupling chemistry, such Stille, Kumada, Negishi coupling methods, and the like, may be employed to prepare desired products 2 or 6.

Scheme II

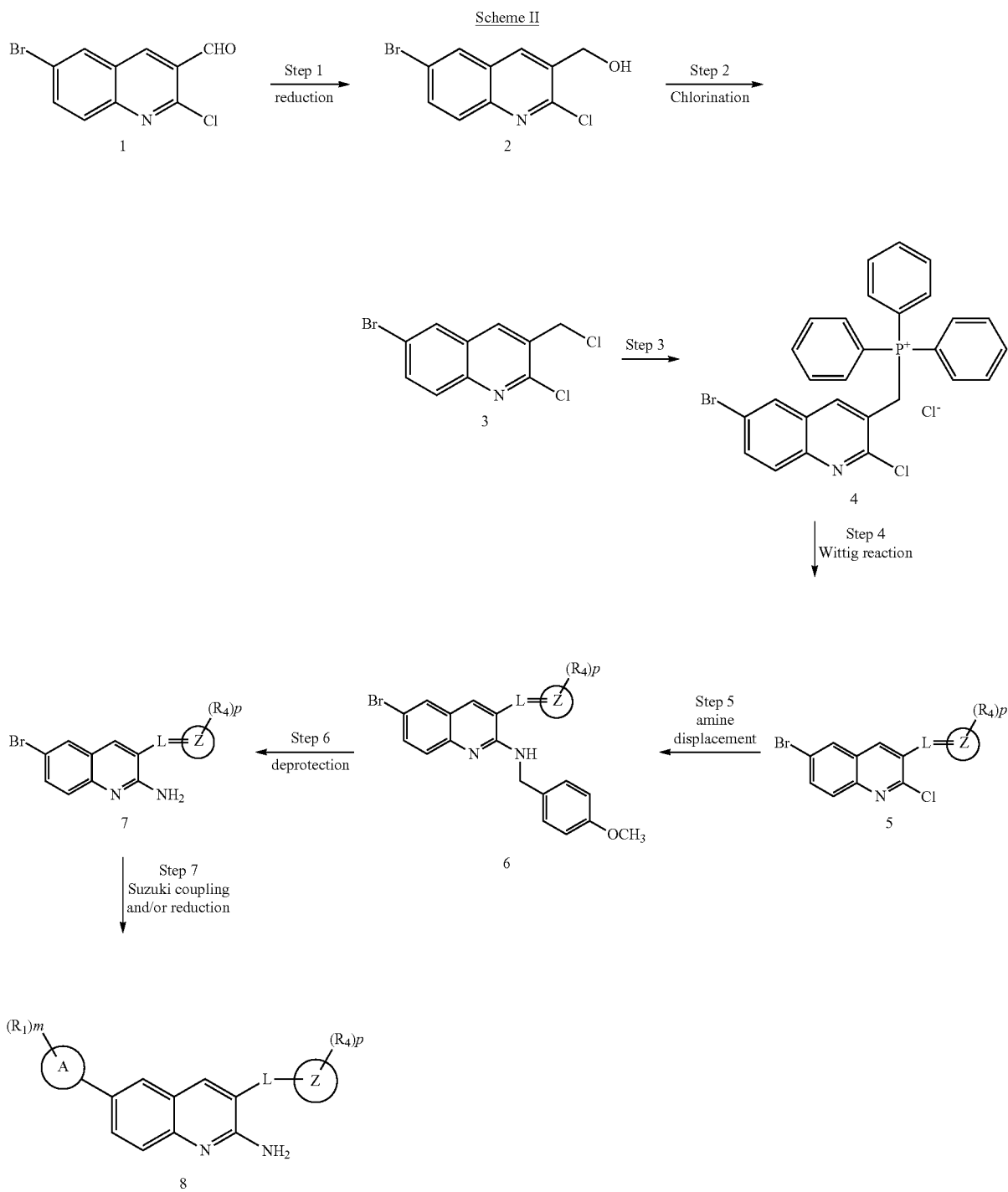

Compounds 8 in scheme II, of formulas I, I-A and I-B, may be prepared by the method illustrated in scheme II and described step-by-step below.

The aldehyde of Bromo-chloro quinoline 1 (may be purchased or made separated by known published methods) may be reduced using known reducing agents and methods, such as use of a borohydride, to afford the corresponding alcohol 2. Alcohol 2 can be converted to the corresponding chloride 3 using a suitable source of chloride, such as thionyl chloride. Chloride 3 can be activated as the triphenyl-phosphine adduct 4, as shown above. Intermediate 4 may be reacted with the desired aldehyde under Wittig reactions conditions to provide the product 5. The amine may be installed by direct displacement of the chloride in 5 to afford the amino-protected intermediate 6, which can be deprotected to afford compound 7. The bromide of intermediate 7 can then be reacted in Suzuki or Suzuki-like fashion, as described above in scheme 1, to afford the desired product having the double bond in tact (not shown), and it may then be reduced to afford the final product 8.

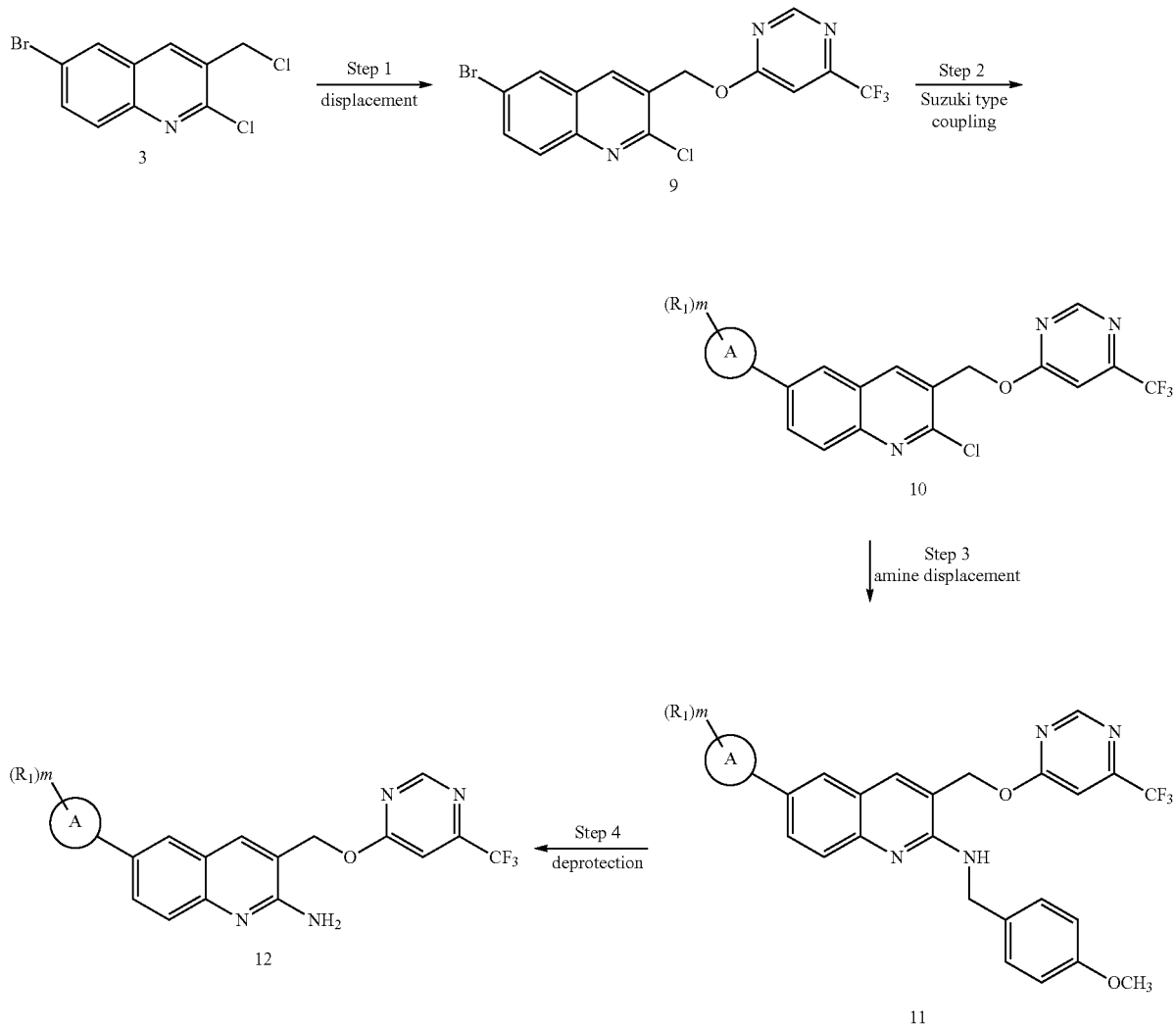

Compounds 12 in scheme III, of formulas I, I-A and I-B, may be also prepared by the method illustrated in scheme III and described step-by-step below.

The chloride of the bromo-chloro quinoline 3 (scheme II) may be displaced with a pyrimidine alcohol using known reducing agents and methods to afford the corresponding adduct 9. The bromide of 9 can then be reacted in Suzuki or Suzuki-like fashion, as described above in scheme 1, to afford the chloride intermediate 10. The chloride can then be displaced with a protected amine as shown in intermediate 11, followed by deprotection to provide the final desired compound 12.

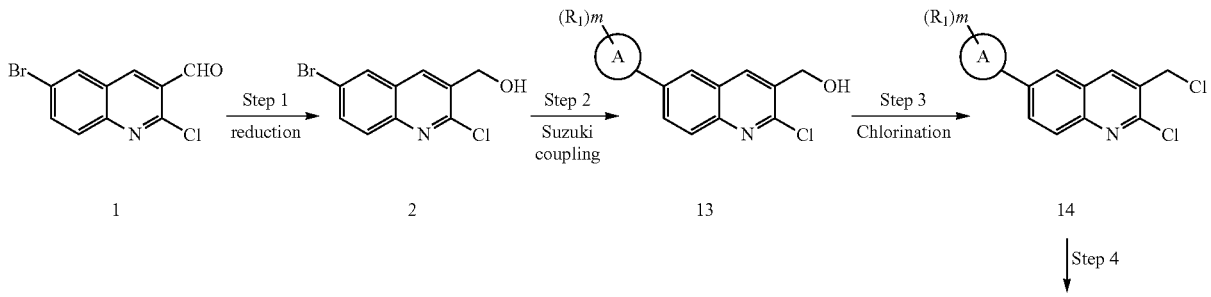

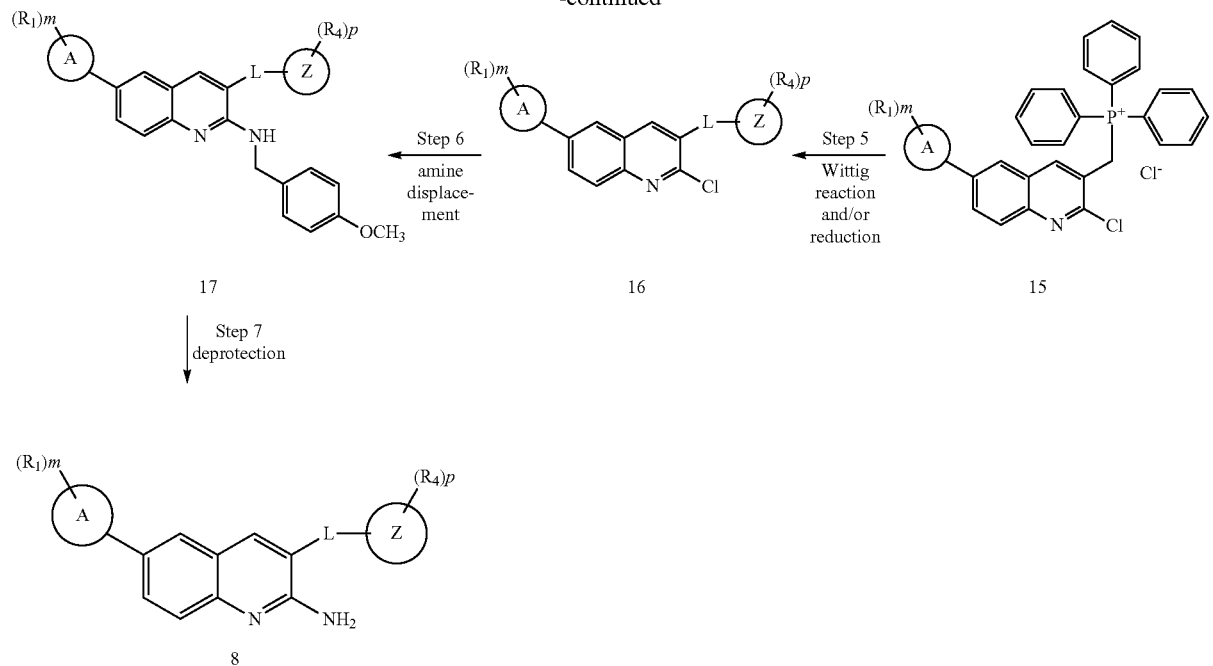

Compounds 8 in scheme IV, of formulas I, I-A and I-B, may be also prepared by the method illustrated in scheme IV and described step-by-step below.

The aldehyde of bromo-chloro quinoline 1 (may be purchased or made separated by known published methods) may be reduced using known reducing agents and methods, such as use of a borohydride, to afford the corresponding alcohol 2. The bromide of alcohol 2 can then be reacted in Suzuki or Suzuki-like fashion, as described above in scheme 1, to afford the chloride intermediate 13. The alcohol of 13 can then be converted to the corresponding chloride using a suitable chloride source, such as thionyl chloride or $POCl_3$, to provide the corresponding chloride 14. Chloride 14 can then be carried through steps 3, 4, 5 and 6 of scheme II to afford final products 8.

Scheme V

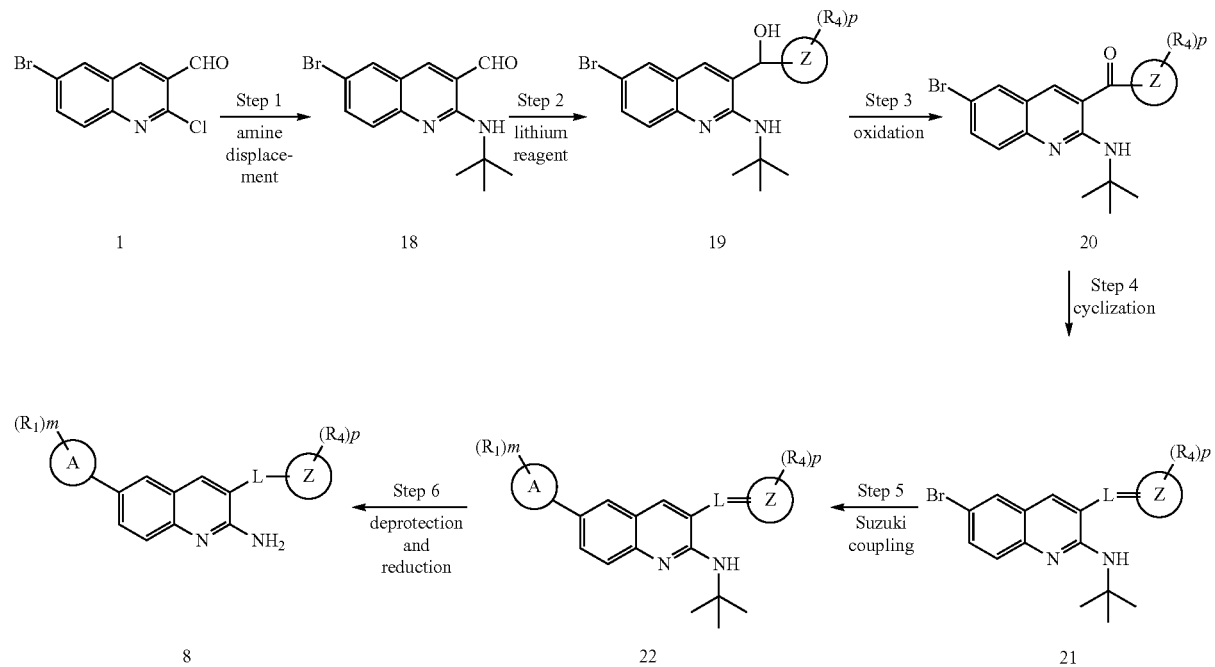

Alternatively, compounds 8 in scheme V, of formulas I, I-A and I-B, may be prepared by the method illustrated in scheme V and described step-by-step below.

The chloride of bromo-chloro quinoline aldehyde 1 may be displaced by a protected amine as shown, to provide intermediate 18. Compound 18 can be reacted with a lithiated ring group Z, desirably substituted, to afford the corresponding alcohol 19. Intermediate 19 may be oxidized to the corresponding ketone 20 by conventional methods. The ketone 20 can be converted to the corresponding intermediate 21 using known methods. Compound 21 may then be treated successively with steps taught and disclosed in schemes II-IV to afford compounds 8.

Scheme VI

Alternatively, compounds 8 in scheme VI, of formulas I, I-A and I-B, may be prepared by the method illustrated in scheme VI and described step-by-step below.

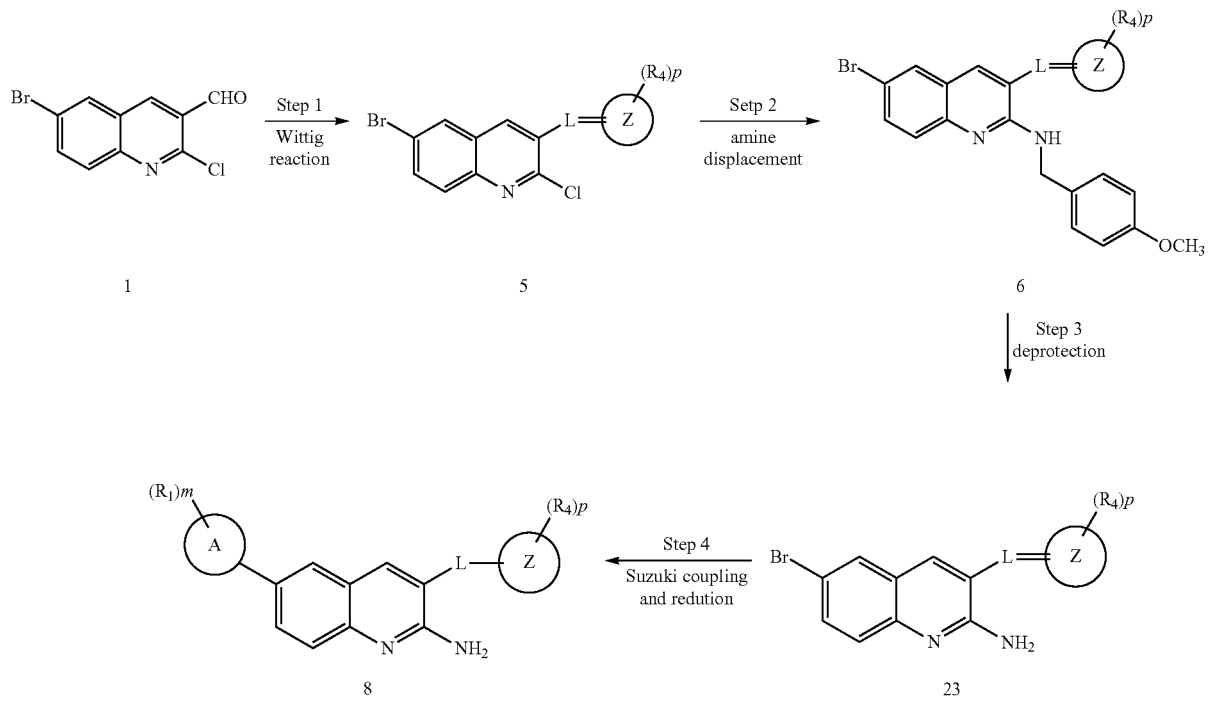

The chloride of bromo-chloro quinoline aldehyde 1 may be displaced in a Wittig fashion as shown in step 4 of scheme II to provide compound 6. Compound 6 may then be deprotected to afford intermediate 23, which can be subjected to a Suzuki or Suzuki-like coupling reaction to provide finally desired compounds 8.

Scheme VII

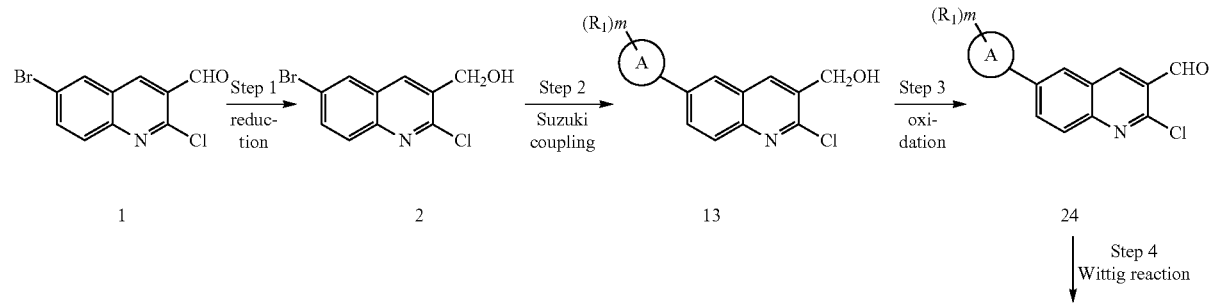

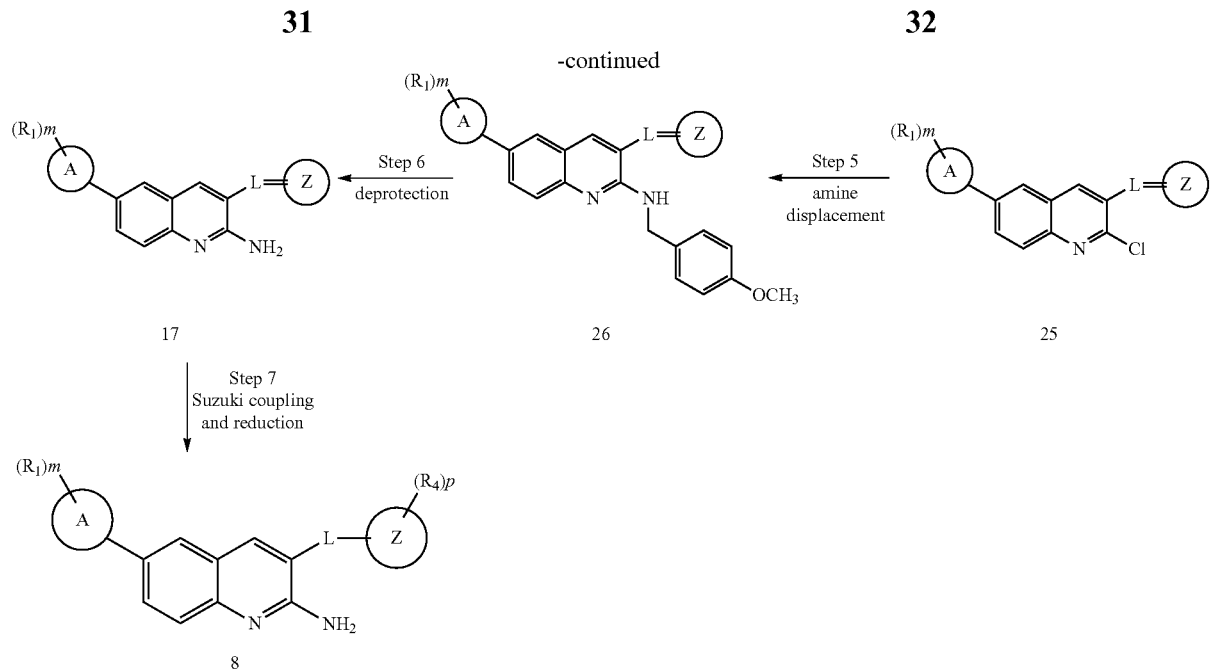

Alternatively, compounds 8 in scheme VII, of formulas I, I-A and I-B, may be prepared by the method illustrated in scheme VII wherein desired $R^4$ group(s) on ring Z may be effectively installed last, as described step-by-step below.

The aldehyde of bromo-chloro quinoline aldehyde 1 may be reduced using conventional methods, such as with a borohydride under suitable conditions to afford the corresponding alcohol 2. Compound 2 may then be subjected to a Suzuki or Suzuki-like coupling reaction to provide compounds 13. Compound 13 can be reacted in a Wittig fashion as shown in step 4 of scheme II to provide compound 25. The chloride of compound 25 may then be displaced with a suitably protected amine to afford 26. Compound 26 may be deprotected to afford intermediate 27, which can be subjected to a Suzuki or Suzuki-like coupling reactions to install desired groups $R^4$ and provide finally desired compounds 8.

EXAMPLES

The Examples, described herein below, represent various exemplary starting materials, intermediates and compounds of Formulas I, I-A and I-B, which should assist in a better understanding and appreciation of the scope of the present invention and of the various methods which may be used to synthesize compounds of Formulas I, I-A and I-B. It should be appreciated that the general methods above and specific examples below are illustrative only, for the purpose of assistance and of understanding the present invention, and should not be construed as limiting the scope of the present invention in any manner. The exemplary compounds disclosed herein have been named using either (1) the naming convention provided with Chem-Draw Ultra software, available in Chem Office, or (2) by the ISIS database software (Advanced Chemistry Design Labs or ACD software).

Chromatography:

Unless otherwise indicated, crude product-containing residues were purified by passing the crude material or concentrate through an ISCO brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

Example 1

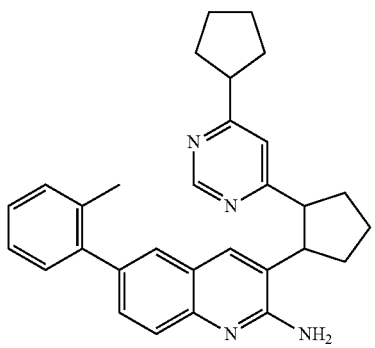 [SMILES: Cc1ccccc1-c1ccc2nc(N)c(C3CCCC3c3cc(C4CCCC4)ncn3)cc2c1]

Synthesis of 3-(2-(6-cyclopentylpyrimidin-4-yl)cyclopentyl)-6-o-tolylquinolin-2-amine Step 1:
To a solution of 6-bromoquinolin-2-amine (5.0 g, 22 mmol), o-tolylboronic acid (4.3 g, 31 mmol), saturated sodium carbonate (2.5 ml, 22 mmol) and nBuOH (50 ml, 546 mmol) under $N_2$ was added dichlorobis(triphenyl-phosphine)palladium (II) (1.6 g, 2.2 mmol). The reaction mixture was heated to 55° C. and allowed to stir overnight. The reaction mixture was allowed to cool to RT then was extracted with EtOAc and washed with water and brine (3×) then dried over $MgSO_4$ and concentrated in vacuo to remove solvent. The crude orange solid was dissolved in DCM and loaded onto a chromatography column and eluted with 0-75% EtOAc/Hexane then 100% EtOAc to give 6-o-tolylquinolin-2-amine as light yellow solid.
Step 2:
To a solution of 6-o-tolylquinolin-2-amine (1.0 g, 4.3 mmol) and THF (20 ml, 244 mmol) cooled to 0° C. in an ice-bath under $N_2$, were added simultaneously dropwise via separate addition funnels pivaloyl chloride (0.51 ml, 4.3 mmol) in THF (10 ml, 122 mmol) and TEA (0.59 ml, 4.3 mmol) in THF (10 ml, 122 mmol). The cloudy yellow solution was allowed to warm to ambient temperature and stirred overnight. The reaction mixture was diluted with EtOAc and washed with water and brine then dried over $MgSO_4$ and concentrated in vacuo to give an oily yellow semi-solid. The crude product was dissolved in DCM and purified by column chromatography (0-25% EtOAc:Hex) to give N-(6-o-tolylquinolin-2-yl)pivalamide as a tacky white foam (1.2 g).
Step 3:
N-(6-o-Tolylquinolin-2-yl)pivalamide (0.93 g) was dissolved in $Et_2O$ (31 ml) under $N_2$ and this solution was cooled to −70° C. and a 1.6 M nBuLi (3.5 ml, 8.8 mmol) in hexane was added dropwise. The mixture was then stirred at 0° C. for 3 h. Iodine (0.93 g, 3.7 mmol) in $Et_2O$ (7.9 ml) was introduced at −70° C., allowed to warm to −50° C. for 1 h. The reaction was quenched with water and extracted with EtOAc. The organic layer was washed with water and brine, then dried over $MgSO_4$ and concentrated in vacuo to give a yellow oil. The crude material was purified by column chromatography (5-60% EtOAc/Hexane) to give N-(3-iodo-6-o-tolylquinolin-2-yl)pivalamide as a yellow oil.
Step 4:
A flask containing cyclopenten-1-ylboronic acid (4.79 g, 42.8 mmol), 4,6-dichloropyrimidine (6.4 g, 42.8 mmol), potassium acetate (2.5 g, 42.8 mmol), and dichlorobis(4-(di-tert-butylphosphino)-N,N-dimethylaniline)palladium (II) (0.23 g, 0.86 mmol) was stirred under inert atmosphere. Ethanol (99 mL) and water (16.5 mL) were added and the mixture heated to 80° C. After a total of 14 h, the mixture was allowed to cool and partitioned between EtOAc and water. The organic phase was washed with saturated aqueous bicarbonate, water and brine, then concentrated and purified via column chromatography (2-25% EtOAc/hexanes) to afford 4,6-dicyclopentenylpyrimidine.
Step 5:
In a small Smith Synthesizer vial, solid N-(3-iodo-6-o-tolylquinolin-2-yl)pivalamide (0.42 g, 0.94 mmol), 4,6-dicyclopentenylpyrimidine (0.40 g, 1.88 mmol), tri-o-tolylphosphine (0.086 g, 0.28 mmol), and palladium(II) acetate (0.032 g, 0.14 mmol) were combined. The vial was sealed and purged with $N_2$ atmosphere. N-methylpyrrolidone (2.7 mL) and TEA (0.53 mL, 3.8 mmol) were added to the mixture via syringe, and the mixture was heated to 120° C. for 10 h. The mixture was allowed to cool and then diluted in ~150 mL water and extracted with EtOAc. The organic phase was washed with water and brine, then concentrated and purified by silica gel chromatography (5-50% EtOAc/hexanes). The fractions containing N-(3-(2-(6-cyclopentenylpyrimidin-4-yl)cyclopent-2-enyl)-6-o-tolylquinolin-2-yl)pivalamide were concentrated to afford a yellow solid.
Step 6:
A solution of N-(3-(2-(6-cyclopentenylpyrimidin-4-yl)cyclopent-2-enyl)-6-α-tolylquinolin-2-yl)pivalamide (0.070 g, 0.13 mmol) in 1:1 DCM/MeOH (3 mL) was treated with 10% palladium on carbon (0.014 g) and place under hydrogen atmosphere for 2 h. After 2 h, the mixture was then diluted with DCM and filtered through diatomaceous earth. The filtrate was concentrated and the crude material was absorbed onto a plug of silica gel and purified by column chromatography eluting with a gradient of 20-100% EtOAc in hexane. The fractions were concentrated to furnish the product N-(3-(2-(6-cyclopentylpyrimidin-4-yl)cyclopentyl)-6-o-tolylquinolin-2-yl)pivalamide as a mixture of stereoisomers.
Step 7:
In a small Smith synthesizer vial, N-(3-(2-(6-cyclopentylpyrimidin-4-yl)cyclopentyl)-6-o-tolylquinolin-2-yl)pivalamide was treated with MeOH (0.75 mL) and 5N NaOH (250 μL, 1.25 mmol). The vial was sealed and heated to 60° C. for 6 h. The reaction mixture was allowed to cool to ambient temperature and treated with 0.15 mL conc. HCl dropwise, and the mixture was eluted on an SCX cartridge with MeOH followed by 2M $NH_3$/MeOH. The basic fraction was concentrated to afford the titled compound. (ESI, pos. ion) m/z: 449 (M+1).

Example 2

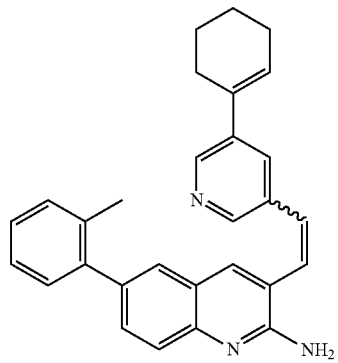 [SMILES: Cc1ccccc1-c1ccc2nc(N)c(C=Cc3cncc(C4=CCCCC4)c3)cc2c1]

Synthesis of 3-(2-(5-cyclohexenylpyridin-3-yl)vinyl)-6-o-tolylquinolin-2-amine

Step 1:
To a suspension of 5-bromo-3-formylpyridine (1.25 g, 6.72 mmol) in EtOH/H$_2$O (6/1, 17.8 mL) was added cyclohexenylboronic acid (1.02 g, 8.06 mmol) and potassium acetate (1.65 g, 16.8 mmol). The solution was degassed three times and dichlorobis(4-(di-tert-butylphosphino)-N,N-dimethylaniline)palladium (II) (0.084 g, 0.13 mmol) was added. The reaction was stirred at 80° C. for 18 h, and cooled to RT. The reaction mixture was concentrated, then triturated in EtOH and filtered. The filtrate was diluted with DCM and washed with water, brine, then concentrated and purified residue by column chromatography (2-25% EtOAc/hexanes). The clean fractions were concentrated to afford 5-cyclohexenylnicotinaldehyde as a tan-colored oil.

Step 2:
6-Bromo-2-chloroquinoline-3-carbaldehyde (6.0 g, 22.2 mmol) was suspended in EtOH (65 mL). The solution was cooled to 0° C. and treated with sodium borohydride (1.26 g, 33.3 mmol). The reaction was warmed to RT and stirred for 40 min. The mixture was quenched with 30 mL saturated NaHCO$_3$ solution and followed by 100 mL H$_2$O. After gas evolution ceased, diluted with 250 mL EtOAc and washed with 2× water, 2× saturated NaHCO$_3$ solution, and 2× brine. The organics were then dried over Na$_2$SO$_4$ and concentrated to afford (6-bromo-2-chloroquinolin-3-yl)methanol as a yellow solid.

Step 3:
(6-Bromo-2-chloroquinolin-3-yl)methanol (4.57 g, 16.8 mmol) was treated with DCM (36.4 ml, 565 mmol) and thionyl chloride (36.4 ml, 498 mmol) at ambient temperature. After 2.5 h, the reaction mixture was concentrated in vacuo and azeotroped with 3×50 mL toluene, to afford 6-bromo-2-chloro-3-(chloromethyl)quinoline as a yellow solid.

Step 4:
The 6-bromo-2-chloro-3-(chloromethyl)quinoline (4.9 g, 16.8 mmol) was suspended in 50 mL toluene and triphenylphosphine (4.4 g, 16.8 mmol) was added. The mixture was heated to reflux for 12 hours. Then it was allowed to cool to ambient temperature and filtered to afford ((6-bromo-2-chloroquinolin-3-yl)methyl)triphenylphosphonium chloride as a tan solid.

Step 5:
Treated a mixture of 5-cyclohexenylnicotinaldehyde (0.25 g) and ((6-bromo-2-chloroquinolin-3-yl)methyl)triphenylphosphonium chloride (0.73 g) with DMSO (0.36 mL) and added potassium carbonate (0.37 g). The suspension was heated to 70° C. for 1 h. The mixture was allowed to cool to ambient temperature and then partitioned between EtOAc and water. The aqueous layer was extracted with 2×EtOAc, washed the combined organics with brine and dried the organic layers over sodium sulfate. Concentrated organics in vacuo and triturated solids with MeOH (5 mL). The precipitate was collected to afford 6-bromo-2-chloro-3-(2-(5-cyclohexenylpyridin-3-yl)vinyl)quinoline as a yellow solid.

Step 6:
Suspended the 6-bromo-2-chloro-3-(2-(5-cyclohexenylpyridin-3-yl)vinyl)quinoline (0.35 g, 0.81 mmol) in N-methylpyrrolidone (3.1 ml, 32.4 mmol) in a vessel and added 4-methoxybenzylamine (0.32 ml, 2.4 mmol). The vessel was heated to 200° C. in microwave for 30 min. N-Methylpyrrolidone solution added slowly to rapidly stirring H$_2$O (60 mL) and the resulting precipitate was filtered. The solid was triturated with Et$_2$O to afford a yellow powder, N-(4-methoxybenzyl)-6-bromo-3-(2-(5-cyclohexenylpyridin-3-yl)vinyl)quinolin-2-amine.

Step 7:
The yellow powder, N-(4-methoxybenzyl)-6-bromo-3-(2-(5-cyclohexenylpyridin-3-yl)vinyl)quinolin-2-amine, was dissolved in TFA (1.5 ml, 19.5 mmol) and heated to 90° C. for 1 h. Removed volatiles in vacuo and then treated residue with 3 mL MeOH. Resulting suspension was loaded directly onto an SCX column and eluted with MeOH followed by 2M NH$_3$ in MeOH. Basic fraction was concentrated to afford 6-bromo-3-(2-(5-cyclohexenylpyridin-3-yl)vinyl)quinolin-2-amine.

Step 8:
To a suspension of 6-bromo-3-(2-(5-cyclohexenylpyridin-3-yl)vinyl)quinolin-2-amine (0.10 g, 0.25 mmol) in EtOH/H$_2$O (6/1, 0.5 mL) was added o-tolylboronic acid (0.042 g, 0.31 mmol) and potassium acetate (0.060 g, 0.62 mmol). The solution was degassed three times and then dichlorobis(4-(di-tert-butylphosphino)-N,N-dimethylaniline)palladium (II) (0.0035 g, 0.0049 mmol) was added. The reaction was heated to 100° C. for 2 h, then cooled to RT. Mixture was diluted with 15 mL H$_2$O and filtered. The precipitate was washed with water then diethyl ether and air-dried to afford a bright yellow solid: 3-(2-(5-cyclohexenylpyridin-3-yl)vinyl)-6-o-tolylquinolin-2-amine.

(ESI, pos. ion) m/z: 418 (M+1).

Example 3

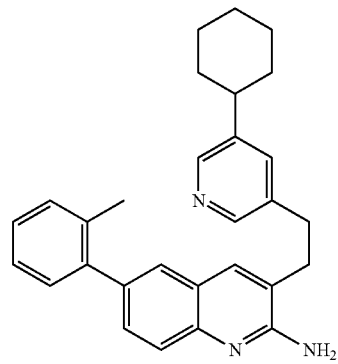 [SMILES: Cc1ccccc1-c1ccc2nc(N)c(CCc3cncc(C4CCCCC4)c3)cc2c1]

Synthesis of 3-(2-(5-cyclohexylpyridin-3-yl)ethyl)-6-o-tolylquinolin-2-amine 3-(2-(5-Cyclohexenylpyridin-3-yl)vinyl)-6-o-tolylquinolin-2-amine (0.031 g, 0.074 mmol) was dissolved in a mixture of EtOH (1.0 mL) and DCM (0.5 mL) in a vessel. The vessel was purged with N$_2$ gas and to the mixture was added a catalytic amount of 10% palladium on carbon. The vessel and mixture was purged with H$_2$ and stirred for 12 h. The mixture was diluted with 2 ml DCM and filtered through two successive 5.0 μm PTFE frits, washing with a total of 10 mL DCM. The filtrate was concentrated in vacuo and th resulting residue was purified by chromatography (2-10% MeOH/DCM) to afford: 3-(2-(5-cyclohexylpyridin-3-yl)ethyl)-6-o-tolylquinolin-2-amine.

(ESI, pos. ion) m/z: 422 (M+1).

Example 4

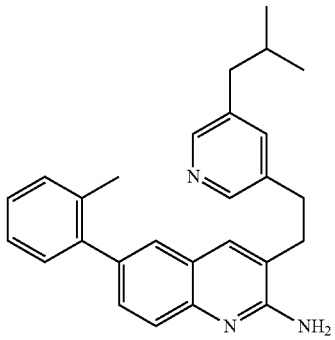 [SMILES: Cc1ccccc1-c1ccc2nc(N)c(CCc3cncc(CC(C)C)c3)cc2c1]

Synthesis of 3-(2-(5-isobutylpyridin-3-yl)vinyl)-6-o-tolylquinolin-2-amine

Step 1:
A mixture of (6-bromo-2-chloroquinolin-3-yl)methanol (19.8 g, 72.5 mmol, prepared as in example 2, step 2), o-tolylboronic acid (10.4 g, 76.1 mmol), potassium acetate (21.3 g, 217.4 mmol) and dichlorobis(4-(di-tert-butylphosphino)-N,N-dimethylaniline)palladium (II) (0.51 g, 0.72 mmol) in $CH_3CN$ (300 ml) and water (100 ml) was heated in to reflux. After 2 h, the reaction was allowed to cool to RT and the aqueous phase was discarded. The organics were washed with 2×50% brine/water, and then 2× brine. The organics were concentrated to ~100 mL, at which point the precipitate was filtered off to afford a pale yellow solid of (2-chloro-6-o-tolylquinolin-3-yl)methanol.

Step 2:
(2-chloro-6-o-tolylquinolin-3-yl)methanol (13.9 g, 49.0 mmol) was treated with DCM (100 ml) and thionyl chloride (106 ml, 1456 mmol) at ambient temperature. After 15 min, the solution was concentrated and azeotroped with 2×100 mL toluene, to afford a yellow solid of 2-chloro-3-(chloromethyl)-6-o-tolylquinoline.

2-Chloro-3-(chloromethyl)-6-o-tolylquinoline (14.8 g, 49.0 mmol) was suspended in 200 mL toluene and treated with triphenylphosphine (16.1 g, 61.2 mmol). The mixture was heated to reflux for 24 h and then stirred at ambient temperature for another 36 h. Another 5.0 g of additional $PPh_3$ was added and the mixture heated to reflux for another 4 h. The resulting suspension was then allowed to cool to ambient temperature and filtered. The precipitate was washed with 50 mL toluene and air-dried to afford 19 g of a white crystalline solid. The filtrate was concentrated to ~¼ volume and heated at reflux for another 3 h, then filtered and air-dried to afford another 4.8 g of white solid, for a total of 23.8 g of ((2-chloro-6-o-tolylquinolin-3-yl)methyl)triphenylphosphonium chloride.

Step 3:
((2-Chloro-6-o-tolylquinolin-3-yl)methyl)triphenylphosphonium chloride (4.0 g, 7.1 mmol) was dissolved in DMSO (25 ml, 354 mmol). Potassium carbonate (2.0 g, 14 mmol) and 5-bromo-3-formylpyridine (1.3 g, 7.1 mmol) were added and the mixture was heated to 70° C. for 1 h. The mixture was cooled to ambient temperature and then partitioned between EtOAc and water. The organic phase was washed with water and brine, the organic layer was dried over sodium sulfate and then concentrated. The residue was triturated with $Et_2O$ and filtered.

The $Et_2O$ filtrate was concentrated in vacuo and the residue was suspended in N-methylpyrrolidone (15 ml) and treated with 4-methoxybenzylamine (3.0 ml, 23 mmol). The mixture was heated to 200° C. for 70 min. The N-methylpyrrolidone solution was added dropwise to a rapidly stirring mixture of 1:1 water/saturated sodium bicarbonate solution, then extracted with 2×EtOAc. The organics were dried over sodium sulfate and concentrated to afford an orange oil.

The oil was dissolved in TFA (10.9 ml) and heated to 90° C. for 1 h. Volatiles were removed in vacuo and then the residue was treated with 100 mL MeOH. The resulting suspension was filtered and the filtrate was concentrated to ~5 mL and dripped into rapidly stirring saturated aqueous sodium bicarbonate. The precipitate was filtered, washed with water and diethyl ether and air-dried to afford 3-(2-(5-bromopyridin-3-yl)vinyl)-6-o-tolylquinolin-2-amine.

Step 4:
Suspended [1,1'-bis(diphenylphosphino)ferrocene]-dichloropalladium(II), complex with DCM (0.039 g) and (Z)-3-(2-(5-bromopyridin-3-yl)vinyl)-6-O— tolylquinolin-2-amine (0.20 g) in THF (0.64 mL) and added isobutylzinc(II) iodide solution in THF (1.92 ml, 0.96 mmol). The vessel was sealed and heated to 80° C. for 16 h. Diluted mixture with EtOAc and 9:1 sat. aq. $NH_4O/NH_4OH$. Washed organics with 9:1 sat. aq. $NH_4Cl/NH_4OH$, water and brine. EtOAc solution was concentrated and the residue purified by chromatography (50-100% EtOAc/hexanes) to afford an off-white solid which was dissolved in 4 mL of 1:1 EtOH/DCM. The solution was treated with 10% Pd/C and placed under $H_2$ atmosphere for 3 h before the mixture was diluted with 10 mL dichloromethane and filtered on two successive 5.0 μm hydrophobic frits, with DCM washes. The solution was concentrated to afford 3-(2-(5-isobutylpyridin-3-yl)ethyl)-6-O— tolylquinolin-2-amine. (ESI, pos. ion) m/z: 416, 418 (M+1).

Example 5

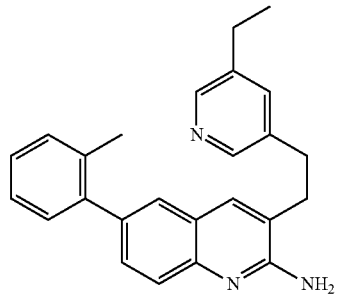 [SMILES: CCc1cncc(CCc2cc3cc(-c4ccccc4C)ccc3nc2N)c1]

Synthesis of 3-(2-(5-ethylpyridin-3-yl)ethyl)-6-o-tolylquinolin-2-amine 3-(2-(5-Bromopyridin-3-yl)vinyl)-6-o-tolylquinolin-2-amine (0.10 g, 0.24 mmol, prepared as in example 4, step 3) was dissolved in THF in a vessel (0.26 ml) to which TEA was added (0.17 ml, 1.2 mmol) followed by trimethylsilylacetylene (0.10 ml, 0.72 mmol). The vessel was purged with argon and then copper (I) iodide (0.0046 g, 0.024 mmol) and bis(triphenylphosphine)palladium (II) chloride (0.0084 g, 0.012 mmol) were added together, in one portion. The vessel was sealed and heated to 50° C. for 30 min. The mixture was diluted with MeOH (4 mL), treated with an excess of potassium carbonate and heated to 50° C. for 1 h. The mixture was filtered and the filtrate concentrated in vacuo. The residue was purified by column chromatography (50-100% EtOAc/hexanes). The product fractions were combined and concentrated, the resulting residue was dissolved in 4 mL of 1:1 EtOH/DCM, treated with 10% Pd/C and subjected to $H_2$ atmosphere overnight. The reaction was then filtered and concentrated. The residue was redissolved in MeOH and loaded onto an SCX cartridge, and the product was eluted with MeOH and then $NH_3$ in MeOH. Basic fraction concentrated and triturated in $Et_2O$, filtered and air-dried to afford: 3-(2-(5-ethylpyridin-3-yl)ethyl)-6-o-tolylquinolin-2-amine. (ESI, pos. ion) m/z: 368 (M+1).

Example 6

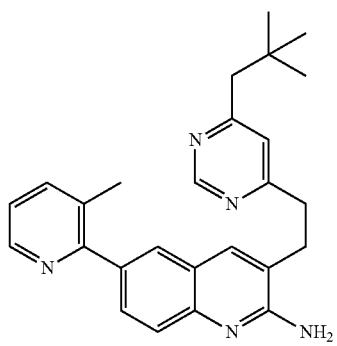 [SMILES: Cc1cccnc1-c1ccc2nc(N)c(CCc3cc(CC(C)(C)C)ncn3)cc2c1]

Synthesis of 3-(2-(5-ethylpyridin-3-yl)ethyl)-6-o-tolylquinolin-2-amine

Step 1:
Suspended 4,6-dichloropyrimidine (1.00 g) and [1,1'-bis(diphenylphosphino)ferrocene]-dichloropalladium(II), complex with DCM (0.55 g) in THF (8.8 ml) and added neopentylzinc(II) iodide solution in THF (20 ml, 10 mmol). The vessel was sealed and heated to 80° C. for 16 h. The mixture was diluted with EtOAc and 9:1 sat. aq. $NH_4Cl/NH_4OH$. The organics were washed with 9:1 sat. aq. $NH_4Cl/NH_4OH$, water and brine, then concentrated and the resulting residue was purified by chromatography (10-30% EtOAc/hexanes), first peak was concentrated to afford a colorless oil of 4-chloro-6-neopentylpyrimidine (0.56 g).
Step 2:
4-Chloro-6-neopentylpyrimidine (0.55 g) was dissolved in DMF (3.3 ml) and treated sequentially with ethynyltrimethylsilane (1.2 ml), TEA (2.1 ml, 15 mmol), copper(I) iodide (0.057 g, 0.30 mmol) and bis(triphenylphosphine)palladium (II) chloride (0.042 g, 0.060 mmol). The resulting suspension was stirred under Ar at 70° C. for 4 h. The mixture was partitioned between EtOAc (100 mL) and water (50 mL). The organic layers were washed with 1× water and 2× brine, dried over $Na_2SO_4$ and concentrated. The crude mixture was purified by chromatography (10-30% EtOAc/hexanes) and the fractions concentrated to afford 4-neopentyl-6-(2-(trimethylsilyl)ethynyl)pyrimidine (0.0.40 g) as a brown oil.
Step 3:
3-Iodo-6-(3-methylpyridin-2-yl)quinolin-2-amine was prepared according to the procedure described in Example 1.
Step 4:
4-Neopentyl-6-(2-(trimethylsilyl)ethynyl)pyrimidine (0.068 g) was dissolved in THF (0.15 ml) in a vessel to which TEA (0.096 ml) was added followed by 3-iodo-6-(3-methylpyridin-2-yl)quinolin-2-amine (0.050 g) and TBAF (~1M in THF) (0.32 ml). The vessel was purged with argon and then copper (I) iodide (0.0026 g, 0.014 mmol) and bis(triphenylphosphine)palladium (II) chloride (0.0049 g, 0.0069 mmol) were added together, in one portion. The vessel was sealed and stirred at ambient temperature for 30 min. The reaction mixture was diluted with water and DCM. The aqueous layer was extracted with an additional portion of DCM and then washed combined organics with 4× water, then concentrated in vacuo. Residue eluted on an SCX cartridge with MeOH followed by 2M $NH_3$ in MeOH. The basic fraction was concentrated and the residue was purified by silica gel chromatography (1-7.5% MeOH/DCM). The clean fractions were combined and concentrated, residue dissolved in 1:1 MeOH/DCM (4 mL), treated with a catalytic amount of 10% Pd/C and subjected to $H_2$ atmosphere. Reaction then filtered and concentrated to afford 6-(3-methylpyridin-2-yl)-3-(2-(6-neopentylpyrimidin-4-yl)ethyl)quinolin-2-amine (0.034 g). (ESI, pos. ion) m/z: 412 (M+1).

Example 7

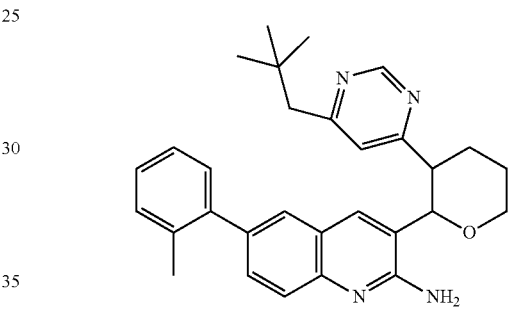

Synthesis of 3-(3-(6-neopentylpyrimidin-4-yl)tetrahydro-2H-pyran-2-yl)-6-O-tolylquinolin-2-amine Step 1:
Added, through an addition funnel, methylmagnesium chloride, 3.0M solution in THF (19.7 mL, 59.1 mmol), dropwise to a solution of 4,6-dichloropyrimidine (8.0 g, 53.7 mmol) and iron tris(acetylacetonate) (0.95 g, 2.68 mmol) in THF (300 mL)/N-Methyl-2-pyrrolidinone (30.0 mL) which was cooled to 0° C. The reaction was allowed to warm to RT and stir 2 h. The reaction mixture was diluted with 10:1 saturated $NH_4Cl/NH_4OH$ and extracted with EtOAc. The combined organic extracts were washed with 10:1 saturated $NH_4Cl/NH_4OH$, water, brine, and dried over $Na_2SO_4$. The solution was filtered and concentrated in vacuo to give the crude material. The crude material was purified by silica gel chromatography by eluting with 1:4 EtOAc in hexane to provide 4-chloro-6-methylpyrimidine.
Step 2:
Dichloro 1,1'-bis(diphenylphosphino)ferrocene palladium (II) (2.2 g, 2.7 mmol) was added to a solution of 4-chloro-6-methylpyrimidine (6.9 g, 53.7 mmol) in neopentylzinc(II) iodide (0.5 M THF)(129 mL, 64.4 mmol). The reaction was refluxed 12 h and then cooled to RT. The reaction mixture was diluted with 10:1 saturated $NH_4Cl/NH_4OH$ and extracted with EtOAc. The combined organic extracts were washed with 10:1 saturated $NH_4Cl/NH_4OH$, water, brine, and dried over $Na_2SO_4$. The solution was filtered and concentrated in vacuo to give the crude material. The crude material was purified by distillation under high vacuum at 70° C. (pot temperature 120° C. to afford 4-methyl-6-neopentylpyrimidine.

Step 3:
N,N-dimethylformamide (54 ml, 0.70 mol) was added dropwise (via a syringe pump) to phosphoryl trichloride (179 ml, 1.96 mol) in a 350 mL sealed tube in an ice bath under nitrogen. After the addition, the water bath was removed and N-(4-bromophenyl)acetamide (60 g, 0.28 mol) was added in one portion and stirred until a homogenous solution was observed (approx. 30 min.). The reaction vessel was sealed and heated at 75° C. for 48 h. The reaction was allowed to cool and slowly poured onto ice (final volume of 2 L) and stirred for 25 min. The solid was filtered and washed with water until the filtrate was no longer acidic (~3 L) and the product was dried in an oven vacuum overnight at 50° C. to afford 6-bromo-2-chloroquinoline-3-carbaldehyde as a light tan colored solid.

Step 4:
6-Bromo-2-chloroquinoline-3-carbaldehyde (10 g, 37 mmol) and 2-methylpropan-2-amine (23 ml, 222 mmol) in N-Methyl-2-pyrrolidone (200 mL) was heated at 130° C. in a sealed tube for 16 h. The mixture was poured into water and the product precipitated. The solid was isolated by filtration and washed with water and dried on vacuum pump overnight to afford 2-(4-methoxybenzylamino)-6-bromoquinoline-3-carbaldehyde Step 5:
Added butyllithium (3.0 mL, 7.6 mmol) to a solution of diisopropylamine (1.3 mL, 9.1 mmol) in THF (15 mL) cooled to −78° C. and then warmed the solution to 0° C. for 15 min before cooling again to −78° C. Added 4-methyl-6-neopentylpyrimidine (1.5 g, 9.1 mmol) in THF (4 mL) slowly and then stirred the solution for 1.5 h at −78° C. Added 6-bromo-2-(tert-butylamino)quinoline-3-carbaldehyde (1.2 g, 3.8 mmol) in THF (6 mL) via syringe and stirred the solution 4 min before quenching it with 2 N HCl (10 mL). The reaction was diluted with EtOAc and the layers were separated. The aqueous layer was extracted with EtOAc. The combined organic extracts were washed with saturated sodium bicarbonate, water, brine, and dried over sodium sulfate. The solution was filtered and concentrated in vacuo to give the crude material, which was purified by silica gel chromatography (2:1 Hex/EtOAc) to afford 1-(6-bromo-2-(tert-butylamino)quinolin-3-yl)-2-(6-neopentylpyrimidin-4-yl)ethanol.

Step 6:
To a solution of 1-(6-bromo-2-(tert-butylamino)quinolin-3-yl)-2-(6-neopentylpyrimidin-4-yl)ethanol (4.0 g, 8.5 mmol) in DCM (10 mL) was added a potassium bromide (0.10 g, 0.85 mmol) solution in water (10 mL) and the biphasic mixture was cooled to 0° C. 2,2,6,6-Tetramethylpiperidine-1-oxyl (0.013 g, 0.085 mmol) was added followed by dropwise addition of a solution of sodium hypochlorite (9.6 mL, 9.3 mmol) (commercial bleach) with sodium hydrogencarbonate (0.16 g, 2.0 mmol) to the mixture via addition funnel. The reaction was stirred 45 min and was quenched by the addition of aqueous sodium sulfite and diluted with EtOAc. The layers were separated and the aqueous was extracted with EtOAc. The combined organics were washed with 1N HCl, water, brine, dried over sodium sulfate, filtered, and concentrated to afford 1-(6-bromo-2-(tert-butylamino)quinolin-3-yl)-2-(6-neopentylpyrimidin-4-yl)ethanone which was used without further purification.

Step 7:
A mixture of 1-(6-bromo-2-(tert-butylamino)quinolin-3-yl)-2-(6-neopentylpyrimidin-4-yl)ethanone (1.0 g, 2.1 mmol), potassium carbonate (0.74 g, 5.3 mmol), and 1-bromo-3-chloropropane (0.23 mL, 2.34 mmol) in acetone (20 mL) was refluxed for 12 hours until a sample analysis by LC/MS showed a complete reaction. The mixture was concentrated and the resulting crude material was diluted with EtoAc and water. The layers were separated and the aqueous layer was extracted with DCM. The combined organic layers were washed with water, brine, dried over sodium sulfate, filtered, and concentrated to afford the crude product. The crude material was purified by silica gel chromatography by eluting with 1:2 to 2:1 EtOAc in hexane to provide 6-bromo-N-tert-butyl-3-(5-(6-neopentylpyrimidin-4-yl)-3,4-dihydro-2H-pyran-6-yl)quinolin-2-amine as an oil.

Step 8:
A-Phos (0.040 g, 0.057 mmol) and potassium acetate (0.22 g, 2.28 mmol) were added to 6-bromo-N-tert-butyl-3-(5-(6-neopentylpyrimidin-4-yl)-3,4-dihydro-2H-pyran-6-yl)quinolin-2-amine (0.58 g, 1.14 mmol) in degassed ($N_2$) Ethanol (11 mL)/Water (1.8 mL). The reaction was evacuated and flushed with $N_2$ gas three times before being refluxed. After 12 h, the reaction was allowed to cool and was diluted with 10:1 saturated $NH_4Cl/NH_4OH$ and extracted with $CH_2Cl_2$. The combined organic extracts were washed with 10:1 saturated $NH_4Cl/NH_4OH$, water, brine, and dried over $Na_2SO_4$. The solution was filtered and concentrated in vacuo to give the crude material. The crude material was purified by silica gel chromatography by eluting with 1:2 EtOAc in hexane, to provide N-tert-butyl-3-(5-(6-neopentylpyrimidin-4-yl)-3,4-dihydro-2H-pyran-6-yl)-6-α-tolylquinolin-2-amine.

Step 9:
N-tert-Butyl-3-(5-(6-neopentylpyrimidin-4-yl)-3,4-dihydro-2H-pyran-6-yl)-6-α-tolylquinolin-2-amine (0.13 g, 0.25 mmol) was heated in TFA (1.5 mL, 19.5 mmol) for 5 h before being concentrated. The crude material was dissolved in $CH_2Cl_2$ and washed with sat'd $NaHCO_3$. The aqueous layers were back extracted with $CH_2Cl_2$ and the combined organic extracts were washed with brine, and dried over $Na_2SO_4$. The solution was filtered and concentrated in vacuo to give the crude material of 3-(5-(6-neopentylpyrimidin-4-yl)-3,4-dihydro-2H-pyran-6-yl)-6-o-tolylquinolin-2-amine taken directly for the next reaction.

Step 10:
10% Palladium on carbon (0.46 g, 0.43 mmol) was added to a solution of 3-(5-(6-neopentylpyrimidin-4-yl)-3,4-dihydro-2H-pyran-6-yl)-6-o-tolylquinolin-2-amine (0.10 g, 0.22 mmol) in EtOH (4.0 mL) which had been degassed with nitrogen. The resulting mixture was degassed briefly with nitrogen and then degassed with hydrogen through a balloon. The reaction was stirred 24 h under a balloon of hydrogen. After 24 h, the reaction demonstrated only a small amount of reduction and was flushed with nitrogen gas. The reaction is transferred to a par shaker and is hydrogenated for 18 h at 60 psi. The reaction was degassed with nitrogen and an additional amount of palladium on carbon (0.46 g, 0.43 mmol) is added. The reaction is hydrogenated at 60 psi for another 24 h and then degassed with nitrogen and then filtered through a pad of celite with EtOH and EtOAc. The crude product was then purified by prep-TLC (20:1 DCM/MeOH 2M $NH_3$). The product was isolated as a single diastereomer as the racemic mixture 3-(6-neopentylpyrimidin-4-yl)tetrahydro-2H-pyran-2-yl)-6-o-tolylquinolin-2-amine. (ESI, pos. ion) m/z: 467 (M+1).

Example 8

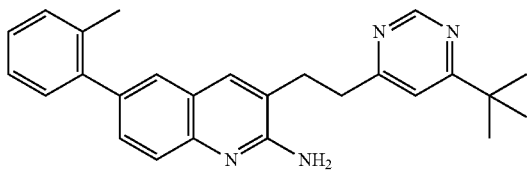 [SMILES: Cc1ccccc1-c1ccc2nc(N)c(CCc3cc(C(C)(C)C)ncn3)cc2c1]

Synthesis of 3-(2-(6-tert-butylpyrimidin-4-yl)ethyl)-6-o-tolylquinolin-2-amine

Step 1:

Cyanocopper (1.9 g, 21.5 mmol) and lithium chloride (1.8 g, 42.9 mmol) were stirred in THF (30 mL) until dissolved (approximately 20 min) and then cooled to 0° C. Next, tert-butyllithium (12.6 mL, 21.5 mmol) was slowly added the resulting solution was stirred at 0° C. for 25 min before cooling to −78° C. 4-Chloro-6-methylpyrimidine (2.3 g, 17.9 mmol) in THF (5 mL) was added and the reaction was allowed to warm to RT over 12 h. The reaction mixture was diluted with 10:1 saturated $NH_4Cl/NH_4OH$ and extracted with EtOAc. The combined organic extracts were washed with 10:1 saturated $NH_4Cl/NH_4OH$, water, brine, and dried over $Na_2SO_4$. The solution was filtered and concentrated in vacuo. The crude material was purified by silica gel chromatography by eluting with 1:4 EtOAc in hexane to provide 4-tert-butyl-6-methylpyrimidine.

Step 2:

A solution of N-butyllithium solution, 2.5M in hexanes (5.2 mL, 13.0 mmol) was added to a solution of diisopropylamine (2.2 mL, 15.6 mmol) in THF (15 mL) cooled to −78° C. After the addition, the solution was warmed to 0° C. for 15 min before cooling again to −78° C. Then 4-tert-butyl-6-methylpyrimidine (2.0 g, 13.0 mmol) in THF (4 mL) was slowly added and then the reaction was stirred for 1.5 h at −78° C. 6-bromo-2-(tert-butylamino)quinoline-3-carbaldehyde (2.0 g, 6.51 mmol) in THF (6 mL) was then added via syringe and stirred 15 min before quenching with saturated $NH_4Cl$. The reaction was diluted reaction with EtOAc and the layers were separated. The aqueous layer was extracted with ethyl acetate and brine, and dried over $Na_2SO_4$. The solution was filtered and concentrated in vacuo to give the crude material. Purification by silica gel chromatography (2:1 Hex/EtOAc) afforded 1-(6-bromo-2-(tert-butylamino)quinolin-3-yl)-2-(6-tert-butylpyrimidin-4-yl)ethanol.

Step 3:

Trifluoroacetic anhydride (1.5 mL, 2.0 mmol) was added to a solution of 1-(6-bromo-2-(tert-butylamino)quinolin-3-yl)-2-(6-tert-butylpyrimidin-4-yl)ethanol (0.46 g, 1.0 mmol) in Pyridine (6 mL) at 0° C. The reaction mixture was allowed to warm to RT and then heated at 50° C. for 6 h. The reaction was concentrated and dissolved in a minimal amount of DCM and purified by passing through a plug of silica gel and eluting with 10:1 Hex/EtOAc to afford (E)-6-bromo-N-tert-butyl-3-(2-(6-tert-butylpyrimidin-4-yl)vinyl)quinolin-2-amine.

Step 4:

A-Phos (0.054 g, 0.076 mmol) and potassium acetate (0.30 g, 3.1 mmol) were added to (E)-6-bromo-N-tert-butyl-3-(2-(6-tert-butylpyrimidin-4-yl)vinyl)quinolin-2-amine (0.67 g, 1.53 mmol) in degassed ($N_2$) solution of ethanol (12 mL)/water (2 mL). The reaction was evacuated and flushed with $N_2$ gas three times before being refluxed. After 12 h the reaction was allowed to cool and was diluted with 10:1 saturated $NR_1Cl/NR_4OH$ and extracted with $CH_2Cl_2$. The combined organic extracts were washed with 10:1 saturated $NH_4Cl/NH_4OH$, water, brine, and dried over $Na_2SO_4$. The solution was filtered and concentrated in vacuo to give the crude material. The crude material was purified by silica gel chromatography by eluting with 1:2 EtOAc in hexane to provide (E)-N-tert-butyl-3-(2-(6-tert-butylpyrimidin-4-yl)vinyl)-6-o-tolylquinolin-2-amine.

Step 5:

(E)-N-tert-butyl-3-(2-(6-tert-butylpyrimidin-4-yl)vinyl)-6-o-tolylquinolin-2-amine (0.10 g, 0.22 mmol) was stirred in TFA (1.0 mL, 13.0 mmol) for 3.5 h and concentrated. The crude material was dissolved in $CH_2Cl_2$ and washed with saturated $NaHCO_3$. The aqueous layers were back extracted with $CH_2Cl_2$ and the combined organic extracts were washed with saturated NaCl, and dried over $Na_2SO_4$. The solution was filtered and concentrated in vacuo to give the crude material taken directly for the next reaction. The crude material was dissolved in ethanol (2.0 mL) and was degassed with nitrogen. 10% Pd/C (0.024 g, 0.22 mmol) was added and the resulting mixture is degassed briefly with nitrogen and then degassed with hydrogen through a balloon. The reaction was stirred 3 h under a balloon of hydrogen and then degassed with nitrogen and filtered through celite with ethyl acetate. The crude product was purified by silica gel chromatography (20:1 Dichlormethane/MeOH 2M $NH_3$) to provide 3-(2-(6-tert-butylpyrimidin-4-yl)ethyl)-6-o-tolylquinolin-2-amine. (ESI, pos. ion) m/z: 397 (M+1).

Example 9

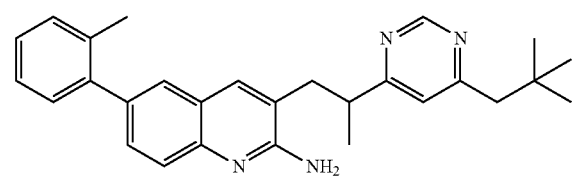 [SMILES: Cc1ccccc1-c1ccc2nc(N)c(CC(C)c3cc(CC(C)(C)C)ncn3)cc2c1]

Synthesis of 3-(2-(6-neopentylpyrimidin-4-yl)propyl)-6-o-tolylquinolin-2-amine

Step 1:

(Acetylacetonato) iron(III) (0.18 g, 0.52 mmol) and 4,6-dichloropyrimidine (1.55 g, 10.4 mmol) were dissolved in a mixture of THF (10 mL) and N-methylpyrrolidinone (1 mL) and placed in an ice bath. 2,2-Dimethylpropylmagnesium chloride, 1.0M solution in diethyl ether (11.44 mL, 11.44 mmol) was added slowly over 5 min. After 15 min saturated ammonium chloride was added to quench and the mixture was extracted with EtOAc (100 mL). The organic was washed with water (2×100 mL) then dried with magnesium sulfate and evaporated to dryness under reduced pressure. Purification using silica chromatography (hexane to dichloromethane gradient) gave 4-chloro-6-neopentylpyrimidine.

Step 2:
4-Chloro-6-neopentylpyrimidine (1.5 g, 8.0 mmol), tributyl (1-ethoxyvinyl)tin (2.7 ml, 8.0 mmol) and bis(4-(di-tert-butylphosphino)-N,N-dimethylaniline)dichloropalladium (II) (0.28 g, 0.40 mmol) were dissolved in dry DMF (20 mL) and heated to 80° C. The mixture was stirred for 24 h then water (200 mL) and EtOAc (200 mL) were added and the phases mixed and separated. The organic layer was dried with magnesium sulfate and evaporated to dryness under reduced pressure. The crude was diluted with hexane (100 mL) and methanol (100 mL) and the phases mixed and separated. The hexane fraction was discarded and the methanol fraction evaporated to dryness under reduced pressure. Purification using column chromatography (hexane to ethyl acetate gradient) gave 4-(1-ethoxyvinyl)-6-neopentylpyrimidine (1.1 g). The material was dissolved in a mixture of tetrahydrofuran (30 mL) and 5 N HCl (10 mL) and stirred for 1 h. Ethyl acetate (200 mL) and water (200 mL) were added, and the phases were mixed and separated and the organic dried with magnesium sulfate before evaporating to dryness under reduced pressure. The crude 1-(6-neopentylpyrimidin-4-yl)ethanone (0.87 g) was used directly without purification.

Step 3:
1-(6-neopentylpyrimidin-4-yl)ethanone (0.87 g, 4.5 mmol) and ((6-bromo-2-chloroquinolin-3-yl)methyl)triphenylphosphonium chloride (2.5 g, 4.5 mmol; prepared as in Example 2, Step 4) were dissolved in dry THF (80 mL) and treated with 1,1,3,3-tetramethylguanidine (0.74 ml, 5.9 mmol). The reaction was heated to 60° C. for 2.5 h and then evaporated to dryness under reduced pressure and purified by column chromatography (hexane to ethyl acetate gradient). The alkene was dissolved in N-methylpyrrolidinone (1 mL) and treated with excess 4-methoxybenzylamine (0.15 ml, 1.1 mmol) then heated in the microwave to 150° C. for 30 min. The reaction solution was partoned between water (100 mL) and ethyl acetate (50 mL). The organic was dried with magnesium sulfate and evaporated to dryness under reduced pressure. Purification with column chromatography (hexane to ethyl acetate gradient) gave the desired (E)-N-(4-methoxybenzyl)-6-bromo-3-(2-(6-neopentylpyrimidin-4-yl)prop-1-enyl) quinolin-2-amine.

Step 4:
(E)-N-(4-methoxybenzyl)-6-bromo-3-(2-(6-neopentylpyrimidin-4-yl)prop-1-enyl)quinolin-2-amine (0.025 g, 0.046 mmol), potassium acetate (0.0029 ml, 0.046 mmol), o-tolylboronic acid (0.0075 g, 0.055 mmol) and the palladium catalyst (0.033 g, 0.046 mmol) were suspended in ethanol (30 mL) and water (5 mL) and heated to 70° C. After 2 h the solution was evaporated to dryness under reduced pressure and partioned between ethyl acetate (100 mL) and water (100 mL). The organic was dried with magnesium sulfate and evaporated to dryness under reduced pressure. The crude was dissolved in DCM (20 mL) and methanol (20 mL) and treated with palladium on carbon (10% by wt, 0.23 g). The mixture was hydrogenated under 60 psi overnight, then filtered through a pad of celite and evaporated to dryness under reduced pressure. The crude material was dissolved in TFA (30 mL) and heated to 70° C. for 1 h. The reaction mixture was evaporated to dryness under reduced pressure. The crude was free based using dichloromethane and saturated sodium bicarbonate then purified by column chromatography (0-10% methanol in DCM gradient) to give 3-(2-(6-neopentylpyrimidin-4-yl)propyl)-6-o-tolylquinolin-2-amine. (ESI, pos. ion) m/z: 425 (M+1).

Example 10

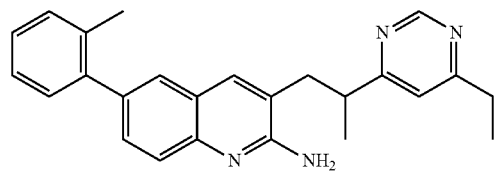 [SMILES: CCc1cc(C(C)Cc2cc3cc(-c4ccccc4C)ccc3nc2N)ncn1]

Synthesis of 3-(2-(6-ethylpyrimidin-4-yl)propyl)-6-o-tolylquinolin-2-amine

Step 1:
4,6-Dichloropyrimidine (3.16 g, 21.2 mmol) and (acetylacetonato)iron(III) (0.75 g, 2.1 mmol) were dissolved in THF (40.0 mL) and N-methylpyrrolidinone (6.0 mL) and placed in a water bath. Ethylmagnesium bromide (3.0M solution in diethyl ether, 17.7 mL, 53.1 mmol) was added slowly. After 5 min saturated ammonium chloride was added to quench the reaction, which was concentrated under reduced pressure to remove the organic solvent. Saturated sodium bicarbonate (30 mL) and ethyl acetate (200 mL) were added and the phases mixed and separated. The organic layer was dried with magnesium sulfate and evaporated to dryness under reduced pressure. Purification using low pressure silica chromatography (hexane to ethyl acetate gradient) gave 4,6-diethylpyrimidine as a yellow oil.

Step 2:
4,6-Diethylpyrimidine (0.94 g, 6.9 mmol) and bromosuccinimide (1.2 g, 6.9 mmol) were suspended in carbon tetrachloride (50 mL) and heated to 70° C. 2,2'-azodiisobutyronitrile (0.052 g, 0.32 mmol) was added and the reaction was refluxed for 1 h. The mixture was cooled, filtered through a sintered glass frit and evaporated to dryness under reduced pressure. Purification using low pressure silica chromatography (hexane to ethyl acetate gradient) gave 4-(1-bromoethyl)-6-ethylpyrimidine.

Step 3:
Triethyl phosphite (3.0 mL, 17.2 mmol) and 4-(1-bromoethyl)-6-ethylpyrimidine (0.66 g, 3.1 mmol) were combined in a reaction flask. Sodium iodide (0.15 g, 1.0 mmol) was added and the mixture heated to 150° C. After 30 min the mixture was cooled. Purification using low pressure silica chromatography (0-10% MeOH in DCM gradient) gave a diethyl 1-(6-ethylpyrimidin-4-yl)ethylphosphonate. The material was dried under high vac at 100° C. for 45 min to remove trace phosphite. 6-Bromo-2-chloroquinoline-3-carbaldehyde (0.51 g, 1.9 mmol) was dissolved in dry THF (40 mL) and added to the phosphonate. Potassium tert-butoxide (0.25 g, 2.3 mmol) was added and the reaction was stirred for 30 min. Saturated ammonium chloride (20 mL) and EtAOc (100 mL) were added and the mixture stirred. Water (100 mL) was added and the phases mixed and separated. The organic was dried with magnesium sulfate and evaporated to dryness under reduced pressure. Purification using low pressure silica chromatography (hexane to EtOAc gradient) gave 6-bromo-2-chloro-3-(2-(6-ethylpyrimidin-4-yl)prop-1-enyl)quinoline.

Steps 4 and 5:
The product from step 3 was taken through a procedure similar to that described in steps 3 and 4 of Example 9, to provide the titled compound, 3-(2-(6-ethylpyrimidin-4-yl)propyl)-6-o-tolylquinolin-2-amine. (ESI, pos. ion) m/z: 383 (M+1).

Example 11

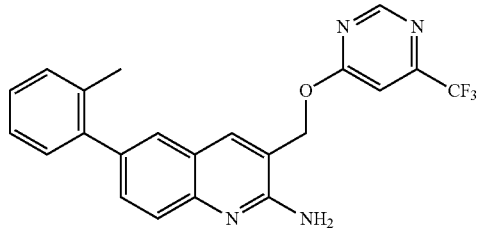 [SMILES: Cc1ccccc1-c1ccc2nc(N)c(COc3cc(C(F)(F)F)ncn3)cc2c1]

Synthesis of 6-o-tolyl-3-((6-(trifluoromethyl)pyrimidin-4-yloxy)methyl)quinolin-2-amine Step 1:
6-Bromo-2-chloro-3-(chloromethyl)quinoline (0.60 g, 2.1 mmol), 6-(trifluoromethyl)-4-pyrimidinol (0.34 g, 2.1 mmol), DIEA (0.54 ml, 3.1 mmol) and sodium iodide (0.31 g, 2.1 mmol) were suspended in CAN (50 mL) and heated to 70° C. for 1 h. The reaction was cooled, diluted with water (100 mL) and extracted with EtOAc (200 mL). After drying with magnesium sulfate the organic was evaporated to dryness under reduced pressure. Purification using low pressure silica chromatography (0-10% methanol in DCM gradient) to give the desired 6-bromo-2-chloro-3-((6-(trifluoromethyl)pyrimidin-4-yloxy)methyl)quinoline.
Step 2 and 3:
The product from step 1 was taken through a procedure similar to that described in steps 3 and 4 of Example 9, to provide the titled compound, o-tolyl-3-((6-(trifluoromethyl)pyrimidin-4-yloxy)methyl)quinolin-2-amine. (ESI, pos. ion) m/z: 411 (M+1).

Example 12

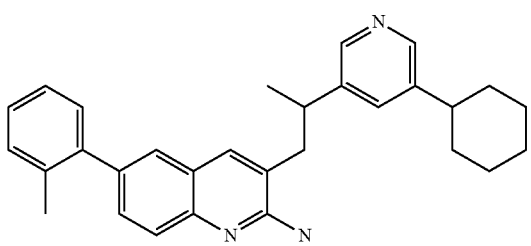 [SMILES: Cc1ccccc1-c1ccc2nc(N)c(CC(C)c3cncc(C4CCCCC4)c3)cc2c1]

Synthesis of 3-(2-(5-cyclohexylpyridin-3-yl)propyl)-6-o-tolylquinolin-2-amine

Step 1:
A mixture of (6-bromo-2-chloroquinolin-3-yl)methanol (19.8 g, 72.5 mmol, prepared as in Example 2, Step 2), o-tolylboronic acid (10.4 g, 76.1 mmol), potassium acetate (21.3 g, 217.4 mmol) and PdCl$_2$(Amphos)$_2$ (0.51 g, 0.72 mmol) in CH$_3$CN (300 ml) and water (100 ml) was heated in to reflux under slightly greater than 1 atm N$_2$. After 2 h, the mixture was then allowed to cool to ambient temperature and the aqueous phase was discarded. The organic layers were washed with 2×50% brine/water, and then 2× brine. The organics were collected and concentrated to ~100 mL, at which point the precipitate was isolated by filtration to afford a pale yellow solid as (2-chloro-6-O— tolylquinolin-3-yl)methanol.
Step 2:
Dissolved (2-chloro-6-o-tolylquinolin-3-yl)methanol (7.0 g, 25 mmol) in DCM (50 ml, 777 mmol) and added manganese dioxide (13 g, 148 mmol). The reaction mixture was stirred overnight. The mixture was filtered through a pad of celite and washed with DCM. The filtrate was concentrated to ~15 mL and loaded onto a silica column which was eluted with dichloromethane to afford 2-chloro-6-o-tolylquinoline-3-carbaldehyde.
Step 3:
Suspended 1-(5-bromopyridin-3-yl)ethanone (3.83 g, 19 mmol) in EtOH (56 ml, 957 mmol) and added sodium borohydride (0.80 g, 21 mmol). The reaction mixture was stirred at ambient temperature for 30 min and then treated mixture with water and aqueous sodium hydroxide. The resulting solution was extracted with 3×DCM. The combined organic layers were washed with brine and then dried over sodium sulfate. The solution was concentrated in vacuo to afford (1-(5-bromopyridin-3-yl)ethanol.
Step 4:
(1-(5-Bromopyridin-3-yl)ethanol was suspended in dichloromethane (10.0 ml, 155 mmol) and added thionyl chloride (10.0 ml, 137 mmol) at ambient temperature for 4 h and then concentrated in vacuo. This material was azeotroped with 2×DCM and 2× toluene to afford a hygroscopic white solid as 3-bromo-5-(1-chloroethyl)pyridine hydrochloride.
Step 5:
3-Bromo-5-(1-chloroethyl)pyridine hydrochloride was treated with 25 mL dioxane, triphenylphosphine (5.0 g, 19 mmol), and lithium bromide (1.7 g, 19 mmol) and heated overnight to 120° C. in a sealed vessel. The reaction mixture was decanted and the dioxane layer discarded. The remaining residue was dissolved with alternating water and Et$_2$O. All of these extracts were combined and the phases were separated. The aqueous was washed with 2×Et$_2$O and then neutralized with saturated aqueous sodium bicarbonate and extracted with Et$_2$O. The combined DCM extracts were then washed once with brine, dried over Na2SO4 and concentrated to afford (1-(5-methylpyridin-3-yl)ethyl)triphenylphosphonium chloride.
Step 6:
(1-(5-methylpyridin-3-yl)ethyl)triphenylphosphonium chloride (1.59 g, 3.29 mmol) was suspended in THF (15.0 ml, 183 mmol) and cooled to 0° C. under nitrogen in an ice-water bath. Potassium hexamethyldisilazane (7.38 ml, 3.29 mmol) was added in toluene and saw dark red-orange colored solution. 2-Chloro-6-o-tolylquinoline-3-carbaldehyde (0.928 g, 3.29 mmol) was added in one portion as a solid. After 10 min, the reaction mixture was removed from ice-water bath and allowed to stir at ambient temperature for 90 min. The reaction mixture was treated with minimal saturated ammonium chloride, EtOAc and water. The phases were separated and the organics washed with bicarb and brine, then dried over sodium sulfate and concentrated. The crude material was purified by column chromatography (5-25% EtOAc/hex) to afford 3-(2-(5-bromopyridin-3-yl)prop-1-enyl)-2-chloro-6-o-tolylquinoline.

Step 7:
3-(2-(5-Bromopyridin-3-yl)prop-1-enyl)-2-chloro-6-o-tolylquinoline (0.60 g, 1.3 mmol) was dissolved in NMP (2.6 ml, 27 mmol) and added 4-methoxybenzylamine (0.52 ml, 4.0 mmol). The reaction mixture was heated to 200° C. for 70 min. The reaction mixture was poured into water, then filtered. The solid was collected and dissolved in EtOAc, dried over Na$_2$SO$_4$ and concentrated to afford N-(4-methoxybenzyl)-3-(2-(5-bromopyridin-3-yl)prop-1-enyl)-6-o-tolylquinolin-2-amine.

Step 8:
N-(4-Methoxybenzyl)-3-(2-(5-bromopyridin-3-yl)vinyl)-6-o-tolylquinolin-2-amine (1.69 g, 3.15 mmol) was dissolved in TFA (10.9 ml, 142 mmol) and heated to 90° C. for 1 h. The solvent was removed in vacuo and then treated residue with 160 mL MeOH. The resulting suspension was filtered. The filtrate was then concentrated to ~5 mL and dripped into rapidly stirring saturated bicarb. The precipitate was formed filtered. The solid was washed with water and ether to afford 3-(2-(5-bromopyridin-3-yl)vinyl)-6-o-tolylquinolin-2-amine.

Step 9:
A mixture of 3-(2-(5-bromopyridin-3-yl)vinyl)-6-o-tolylquinolin-2-amine (0.050 g, 0.12 mmol), cyclohexenyl-boronic acid (0.022 g, 0.17 mmol), potassium acetate (0.051 ml, 0.81 mmol) and dichlorobis(tri-t-butylphosphine)palladium (II) (0.0072 g, 0.012 mmol) in CH$_3$CN (0.9 ml) and water (0.3 ml) was heated at 120° C. in microwave for 10 min. The reaction mixture was concentrated and then diluted with EtOAc, washed with water and brine, and dried over Na$_2$SO$_4$. After filtration, the filtrate was concentrated and dried in vacuum to afford crude 3-(2-(5-cyclohexenylpyridin-3-yl)prop-1-enyl)-6-O-tolylquinolin-2-amine. This material 3-(2-(5-cyclohexenylpyridin-3-yl)prop-1-enyl)-6-O-tolylquinolin-2-amine (0.21 g, 0.48 mmol) and palladium, 10 wt. % on activated carbon (0.10 g, 0.94 mmol) in EtOH (10 ml) was stirred under a hydrogen balloon for 15 h. The resulted mixture was filtered through a pad of celite. The filtrate was concentrated and purified by prep. TLC plate to afford the titled compound 3-(2-(5-cyclohexylpyridin-3-yl)propyl)-6-o-tolylquinolin-2-amine as off-white solid.

The following examples in Table I were prepared by methods analogous to those described in schemes I-VII and Examples 1-12 above. Provided also is the mass spectral data and BACE enzyme and cell-based assay data (IC$_{50}$'s in uM ranges) for each example, where available.

TABLE 1

| Ex. No. | Compound Name | Method | Observed MS | BACE1 FRET assay (uM) | HEK cell assay (uM) |
|---|---|---|---|---|---|
| 9 | 3-(2-(6-neopentylpyrimidin-4-yl)propyl)-6-o-tolylquinolin-2-amine | II | 425 | ++++ | +++ |
| 13 | 3-(2-(6-cyclopentylpyrimidin-4-yl)propyl)-6-o-tolylquinolin-2-amine | II | 423 | ++++ | ++ |
| 14 | 6-o-tolyl-3-((6-ethylpyrimidin-4-yloxy)methyl)quinolin-2-amine | III | 371 | + | + |
| 11 | 6-o-tolyl-3-((6-(trifluoromethyl)pyrimidin-4-yloxy)methyl)quinolin-2-amine | III | 410.9 | +++ | + |
| 10 | 3-(2-(6-ethylpyrimidin-4-yl)propyl)-6-o-tolylquinolin-2-amine | VI | 383 | +++ | ++ |
| 15 | 6-(3-methylpyridin-2-yl)-3-(2-(6-neopentylpyrimidin-4-yl)propyl)quinolin-2-amine | II | 426.1 | +++ | +++ |
| 8 | 3-(2-(6-tert-butylpyrimidin-4-yl)ethyl)-6-o-tolylquinolin-2-amine | V | 397.2 | ++++ | ++ |
| 7 | 3-((2R,3R)-3-(6-neopentylpyrimidin-4-yl)tetrahydro-2H-pyran-2-yl)-6-o-tolylquinolin-2-amine and 3-((2S,3S)-3-(6-neopentylpyrimidin-4-yl)tetrahydro-2H-pyran-2-yl)-6-o-tolylquinolin-2-amine | V | 467.1 | ++++ (ave for 2 isomers) | ++ |
| 16 | 3-(2-(6-tert-butylpyrimidin-4-yl)ethyl)-6-(3-methylpyridin-2-yl)quinolin-2-amine | V | 398.2 | +++ | ++ |
| 17 | 3-(2-(1H-indol-2-yl)ethyl)-6-o-tolylquinolin-2-amine | II | 378 | ++ | +++ |
| 18 | 3-(2-(5-isobutylpyridin-3-yl)ethyl)-6-o-tolylquinolin-2-amine | II | 396 | +++ | ++ |
| 6 | 6-(3-methylpyridin-2-yl)-3-(2-(6-neopentylpyrimidin-4-yl)ethyl)quinolin-2-amine | I | 412 | +++ | ++ |
| 1 | 3-(2-(6-cyclopentylpyrimidin-4-yl)cyclopentyl)-6-o-tolylquinolin-2-amine | I | 449 | ++++ | + |
| 19 | 3-(2-(1-benzyl-1H-pyrazol-4-yl)ethyl)-6-o-tolylquinolin-2-amine | II | 419 | +++ | ++ |
| 20 | 6-(3-methylpyridin-2-yl)-3-(2-(6-(tetrahydro-2H-pyran-4-yl)pyrimidin-4-yl)ethyl)quinolin-2-amine | II | 426 | +++ | ++ |
| 21 | 3-(2-(5-neopentylpyridin-3-yl)ethyl)-6-o-tolylquinolin-2-amine | I | 410 | +++ | + |
| 2 | 3-(2-(5-cyclohexenylpyridin-3-yl)vinyl)-6-o-tolylquinolin-2-amine | II | 418 | +++ | + |
| 5 | 3-(2-(5-ethylpyridin-3-yl)ethyl)-6-o-tolylquinolin-2-amine | II | 368 | ++ | ++ |
| 22 | 3-(2-(5-(3,3-dimethylbutyl)pyridin-3-yl)ethyl)-6-o-tolylquinolin-2-amine | II | 424 | +++ | + |
| 23 | 6-o-tolyl-3-(3-(trifluoromethyl)phenethyl)quinolin-2-amine | II | 407 | ++ | + |

TABLE 1-continued

| Ex. No. | Compound Name | Method | Observed MS | BACE1 FRET assay (uM) | HEK cell assay (uM) |
|---|---|---|---|---|---|
| 3 | 3-(2-(5-cyclohexylpyridin-3-yl)ethyl)-6-o-tolylquinolin-2-amine | II | 422 | ++++ | + |
| 24 | 3-(2-(1-cyclohexyl-1H-pyrazol-4-yl)vinyl)-6-o-tolylquinolin-2-amine | II | 409 | ++ | + |
| 25 | 3-(2-(1-cyclohexyl-1H-pyrazol-4-yl)ethyl)-6-o-tolylquinolin-2-amine | II | 411 | ++++ | ++ |
| 26 | 3-(2-(5-(tetrahydro-2H-pyran-2-yl)pyridin-3-yl)propyl)-6-o-tolylquinolin-2-amine | VII | 438.1 | +++ | ++ |
| 27 | 3-(2-(5-cyclohexylpyridin-3-yl)propyl)-6-o-tolylquinolin-2-amine | VII | 436 | ++++ | + |
| 28 | 3-(2-(oxazol-5-yl)ethyl)-6-o-tolylquinolin-2-amine | II | 330 | ++ | + |
| 29 | 3-(2-(pyridin-2-yl)ethyl)-6-o-tolylquinolin-2-amine | II | 340 | ++ | + |
| 30 | 3-(2-(5-cyclopentylpyridin-3-yl)propyl)-6-o-tolylquinolin-2-amine | VII | 422 | ++++ | ++ |
| 31 | 3-(2-(5-(tetrahydro-2H-pyran-2-yl)pyridin-3-yl)ethyl)-6-o-tolylquinolin-2-amine | II | 424 | +++ | ++ |
| 32 | (±)-(2-(2-amino-3-(2-(pyrimidin-5-yl)ethyl)quinolin-6-yl)-3-methylphenyl)(2-methylpyrrolidin-1-yl)methanone | II | 452 | ++++ | ++++ |
| 33 | (2-(2-amino-3-(2-(pyrimidin-5-yl)ethyl)quinolin-6-yl)-3-methylphenyl)(pyrrolidin-1-yl)methanone | II | 438 | ++++ | ++++ |
| 34 | (2-(2-amino-3-((6-(trifluoromethyl)pyrimidin-4-yloxy)methyl)quinolin-6-yl)-3-methylphenyl)(pyrrolidin-1-yl)methanone | III | 508 | +++ | ++ |

The present invention also provides methods for making compounds of Formulas I, I-A and I-B. In another embodiment of the invention, there is provided a method of making a compound of Formula I, the method comprising the step of (a) reacting a compound 17

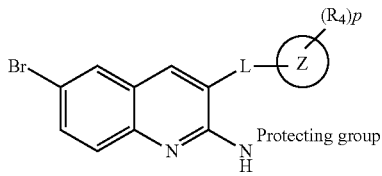

17 wherein L, Z, $R^4$ and p of Formula I are as defined herein, with a compound having the structure

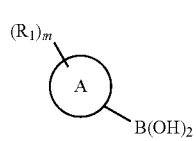

wherein ring A, $R^1$ and m are as defined herein to make a compound 18 of the formula

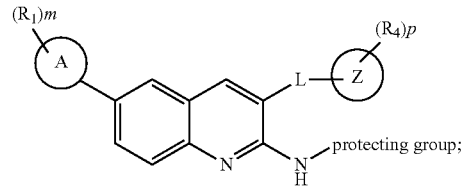

18 and
(b) deprotecting compound 18 to make a compound 19 of formula I

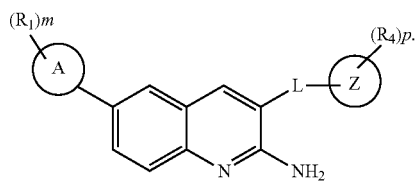

19

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I, I-A and I-B, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

Biological Evaluation

The compounds of the invention may be modified by appending appropriate functionalities to enhance selective biological properties. Surprisingly, the compounds of the present invention exhibit improved pharmacokinetics and pharmacodynamics, which relate, directly and indirectly, to the ability of the compound to be effective for its intended use. For example, the compounds have been found to possess favorable clearance and efflux properties, which readily lend themselves to projecting in-vivo PK and PD properties, which in turn assist in projection of therapeutic target coverage for the compounds and projected efficacious dosages via in-vivo absorption, distribution, metabolism and excretion properties. Increased biological penetration into a given biological compartment (e.g., blood, lymphatic system, central nervous system), increase oral availability, increase solubility to allow administration by injection and alter clearance, metabolism and/or rate of excretion are important factors for discovering which compound may be a useful drug and which may not.

Although the pharmacological properties of the compounds of the invention (Formulas I, I-A and I-B) vary with structural change, in general, activity possessed by compounds of Formulas I, I-A and I-B may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta. In Vitro Enzymatic BACE FRET (Fluorescence Resonance Energy Transfer) Assay (Enzyme Assay Data in Table 1)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. The assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Of the compounds tested, the in-vitro BACE FRET enzyme data for each of Examples 1-33, where available at the time of filing this application, is provided in Table 1. Data key for the in-vitro BACE FRET assay is as follows:

"+" means the compound example has an $IC_{50}$ value of >5.0 uM;

"++" means the compound example has an $IC_{50}$ value in the range from 1.0 uM-5.0 uM;

"+++" means the compound example has an $IC_{50}$ value in the range from 100 nM-1.0 uM;

"+++E" means the compound example has an $IC_{50}$ value in the range less than 100 nM.

In Vitro BACE Cell-Based Assay:

The cell-based assay measures inhibition or reduction of Aβ40 □ in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Of the compounds tested, the cell based assay data for each of Examples 1-33, where available at the time of filing this application, is provided in Table 1. Data key for the cell-based assay is as follows:

"+" means the compound example has an $IC_{50}$ value of >5.0 uM;

"++" means the compound example has an $IC_{50}$ value in the range from 1.0 uM-5.0 uM;

"+++" means the compound example has an $IC_{50}$ value in the range from 500 nM-1.0 uM;

"++++" means the compound example has an $IC_{50}$ value in the range less than 500 nM.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of Abeta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, Abeta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
IV: 5% EtOH, 45% Propylene glycol in 5% Dextrose The compounds of the invention may be shown to reduce the formation and/or deposition of A-beta peptide in the brain or in the cerebrospinal fluid of a mouse or rat.

Indications

Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide and/or plaque on the brain. In one embodiment of the invention, there is provided a method of treating a disorder related to a beta-secretase enzyme in a subject, the method comprising administering to the subject an effective dosage amount of a compound of Formulas I, I-A and I-B. In another embodiment, there is provided a method of reducing production of amyloid beta, and of reducing plaque formation. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I, I-A and I-B. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients and the like as described herein. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the compound is administered by administering a portion of the composition. Alternatively, a pharmaceutical composition in which two or more unit dosages, such as in tablets, capsules and the like, are required to administer an effective amount of the compound may be administered in less than an effective amount for one or more periods of time, for example to ascertain the effective dose for an individual subject, to desensitize an individual subject to potential side effects, to permit effective dosing readjustment or depletion of one or more other therapeutics administered to an individual subject, and/or the like.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hardshell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil; cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I, I-A and I-B with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I, I-A and I-B with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, I-A and I-B may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I:

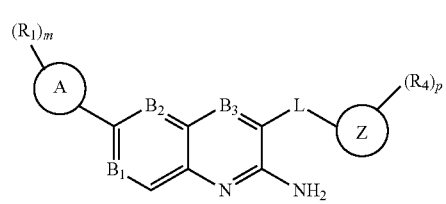

or a stereoisomer or pharmaceutically acceptable salt thereof, wherein

A is a 5- or 6-membered aryl or heteraryl ring;

each of $B^1$, $B^2$ and $B^3$, independently, is N, —CF, —CCH$_3$ or CH;

L is —CR$^2$R$^2$—(CR$^3$R$^3$)—, —CR$^2$R$^2$—O—, —CR$^2$=CR$^3$—, —C≡C—, C$_{3-8}$cycloalkyl, tetrahydrofuranyl or tetrahydropyranyl, wherein the C$_{3-8}$cycloalkyl, tetrahydrofuranyl and tetrahydropyranyl are optionally substituted with 1-4 substituents of R$^4$, and wherein each R$^2$, independently, is H, C$_{1-3}$alkyl or F; and each R$^3$, independently, is H, C$_{1-6}$alkyl, C$_{3-6}$cycloalkyl, —OH, —OC$_{1-4}$alkyl, halo, haloalkyl, CN, —NH$_2$ or —NHC$_{1-6}$alkyl;

each R$^1$ independently, is F, Cl, Br, CF$_3$, OCF$_3$, C$_{1-6}$-alkyl, CN, OH, —OC$_{1-6}$-alkyl, —S(O)$_n$C$_{1-6}$-alkyl, —NH$_2$, CN, —NHC$_{1-6}$-alkyl, —C(O)C$_{1-6}$-alkyl, —C(O)-cycloalkyl or —C(O)NR$^a$R$^b$ wherein R$^a$ is H or C$_{1-6}$alkyl and R$^b$ is R$^4$;

alternatively, R$^a$ and R$^b$ taken together with the nitrogen atom to which they are attached form a 4-7 membered monocyclic heterocycle, wherein the cycloalkyl of the —C(O)-cycloalkyl and monocyclic heterocycle are optionally substituted with 1-3 substituents of R$^4$;

each R$^4$, independently, is halo, haloalkyl, CN, OH, NO$_2$, NH$_2$, acetyl, oxo, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, haloalkoxyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;

Z is a 6-membered monocyclic or 10-membered bicyclic aryl ring or 5- or 6-membered monocyclic or 9-10-membered bicyclic heteraryl ring;

m is 0, 1, 2, 3, 4 or 5;

n is 0, 1 or 2; and p is 0, 1, 2, 3, 4 or 5.

2. The compound of claim 1, or a stereoisomer or pharmaceutically acceptable salt thereof, wherein ring A is a phenyl, pyridine, pyrimidine, triazine or thiophene ring.

3. The compound of claim 1, or a stereoisomer or pharmaceutically acceptable salt thereof, wherein
each of $B^1$, $B^2$ and $B^3$, independently, is —CF, —CCH$_3$ or CH; and
L is —CH$_2$—CH(C$_{1-6}$alkyl)-, —CH$_2$—O—, —CH=CH—, C$_{3-8}$cycloalkyl, tetrahydrofuranyl or tetrahydropyranyl, wherein the C$_{3-8}$cycloalkyl, tetrahydrofuranyl and tetrahydropyranyl are optionally substituted with 1-4 substituents of $R^4$.

4. The compound of claim 3, or a stereoisomer or pharmaceutically acceptable salt thereof, wherein
ring A is a phenyl, pyridine, pyrimidine, triazine or thiophene ring;
each of $B^1$, $B^2$ and $B^3$, independently, is CH;
L is —CH$_2$—CH(C$_{1-6}$alkyl)-, —CH$_2$—O—, —CH=CH—, cyclopropyl, cyclobutyl,
cyclopentyl, cyclohexyl, tetrahydropyranyl or tetrahydrofuranyl, wherein the cyclopropyl, cyclobutyl, cyclopentyl, cyclohexyl, tetrahydropyranyl and tetrahydrofuranyl are optionally substituted with 1-4 substituents of $R^4$; and
Z is a ring selected from phenyl, pyridyl, pyrimidyl, thienyl, furanyl, pyrrolyl, pyrazolyl, imidazolyl, triazolyl, tetrazolyl, thiazolyl, oxazolyl, isothiazolyl, isoxazolyl, diazolyl, thiodiazolyl, oxadiazolyl, pyrazinyl and pyridazinyl, wherein the ring is optionally substituted, independently, with 1-5 substituents of $R^4$.

5. The compound of claim 4, or a stereoisomer or pharmaceutically acceptable salt thereof, wherein
each $R^1$ independently, is F, Cl, CF$_3$, OCF$_3$, methyl, ethyl, CN, OH, —OCH$_3$, —OCF$_3$, —NH$_2$, NHCH$_3$ or —C(O)CH$_3$; and
m is 1 or 2.

6. The compound of claim 1 of formula I-A

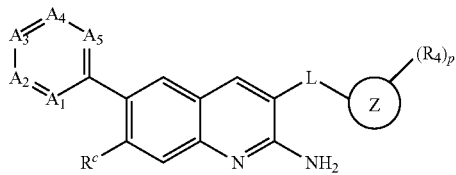

I-A or a stereoisomer or pharmaceutically acceptable salt thereof, wherein
$A^1$ is CR$^1$ or N;
$A^2$ is CR$^1$ or N;
$A^3$ is CR$^1$ or N;
$A^4$ is CR$^1$ or N;
$A^5$ is CR$^1$ or N, provided no more than two of $A^1$, $A^2$, $A^3$, $A^4$ and $A^5$ is N;
each of $R^1$ independently, is H, F, Cl, Br, CF$_3$, OCF$_3$, C$_{1-6}$-alkyl, CN, OH, —OC$_{1-6}$-alkyl, —S(O)$_o$C$_{1-6}$-alkyl, —NH$_2$, CN, —NHC$_{1-6}$-alkyl or —C(O)C$_{1-6}$-alkyl;
R$^c$ is H, C$_{1-3}$alkyl or halo;
L is —CR$^2$R$^2$—(CR$^3$R$^3$)—, —CR$^2$R$^2$—O—, —CR$^2$=CR$^3$—, —C≡C—, C$_{3-8}$cycloalkyl, tetrahydrofuranyl or tetrahydropyranyl, wherein the C$_{3-8}$cycloalkyl, tetrahydrofuranyl and tetrahydropyranyl are optionally substituted with 1-4 substituents of $R^4$, and wherein
each R$^2$, independently, is H, C$_{1-3}$alkyl or F; and each R$^3$, independently, is H, C$_{1-6}$alkyl, C$_{3-6}$cycloalkyl, —OH, —OC$_{1-4}$alkyl, halo, haloalkyl, CN, —NH$_2$ or —NHC$_{1-6}$alkyl;
each R$^4$, independently, is H, halo, haloalkyl, CN, OH, NO$_2$, NH$_2$, acetyl, oxo, C$_{1-10}$-alkyl, C$_{2-10}$-alkenyl, C$_{2-10}$-alkynyl, C$_{3-10}$-cycloalkyl, C$_{2-10}$-cycloalkenyl, C$_{1-10}$-alkylamino-, C$_{1-10}$-dialkylamino-, C$_{1-10}$-alkoxyl, C$_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, haloalkoxyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl;
Z is a ring selected from phenyl, pyridyl, pyrimidyl, thienyl, furanyl, pyrrolyl, pyrazolyl, imidazolyl, triazolyl, tetrazolyl, thiazolyl, oxazolyl, isothiazolyl, isoxazolyl, diazolyl, thiodiazolyl, oxadiazolyl, pyrazinyl, pyridazinyl and indolyl; and
p is 0, 1, 2, 3or 4.

7. The compound of claim 6, or a stereoisomer or pharmaceutically acceptable salt thereof, wherein
each of $A^1$, $A^2$ $A^3$ and $A^5$, independently, is CR$^1$; or
one of $A^1$, $A^2$ $A^3$ and $A^5$, independently, is N and the other four of $A^1$, $A^2$ $A^3$ and $A^5$ is CR$^1$.

8. The compound of claim 7, or a stereoisomer or pharmaceutically acceptable salt thereof, wherein
each R$^4$, independently, is F, Cl, Br, I, CF$_3$, C$_2$F$_5$, haloalkoxyl, C$_{1-6}$-alkyl, CN, OH, OC$_{1-6}$-alkyl, SC$_{1-6}$-alkyl, SC$_{1-6}$-alkyl, S(O)$_o$C$_{1-6}$-alkyl, C$_{3-8}$cycloalkyl, C$_{4-8}$cycloalkenyl, aryl, heteroaryl or heterocyclyl wherein the C$_{3-8}$cycloalkyl,
C$_{4-8}$cycloalkenyl, aryl, heteroaryl and heterocyclyl are optionally substituted independently with 1-5 substituents of F, Cl, Br, haloalkyl, haloalkoxyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, phwnyl, C$_{1-4}$-alkylamino-, C$_{1-4}$-dialkylamino- or C$_{1-4}$-thioalkoxyl.

9. The compound of claim 1, or a stereoisomer or pharmaceutically acceptable salt thereof, selected from
3-(2-(6-cyclopentylpyrimidin-4-yl)cyclopentyl)-6-o-tolylquinolin-2-amine;
3-(2-(5-cyclohexenylpyridin-3-yl)vinyl)-6-o-tolylquinolin-2-amine;
3-(2-(5-cyclohexylpyridin-3-yl)ethyl)-6-o-tolylquinolin-2-amine;
3-(2-(5-isobutylpyridin-3-yl)vinyl)-6-o-tolylquinolin-2-amine;
3-(2-(5-ethylpyridin-3-yl)ethyl)-6-o-tolylquinolin-2-amine;
3-(2-(5-ethylpyridin-3-yl)ethyl)-6-o-tolylquinolin-2-amine;

of 3-(3-(6-neopentylpyrimidin-4-yl)tetrahydro-2H-pyran-2-yl)-6-o-tolylquinolin-2-amine;
3-(2-(6-tert-butylpyrimidin-4-yl)ethyl)-6-o-tolylquinolin-2-amine;
3-(2-(6-neopentylpyrimidin-4-yl)propyl)-6-o-tolylquinolin-2-amine;
3-(2-(6-ethylpyrimidin-4-yl)propyl)-6-o-tolylquinolin-2-amine;
6-o-tolyl-3-((6-(trifluoromethyl)pyrimidin-4-yloxy)methyl)quinolin-2-amine;
3-(2-(6-cyclopentylpyrimidin-4-yl)propyl)-6-o-tolylquinolin-2-amine;
6-o-tolyl-3-((6-ethylpyrimidin-4-yloxy)methyl)quinolin-2-amine;
6-(3-methylpyridin-2-yl)-3-(2-(6-neopentylpyrimidin-4-yl)propyl)quinolin-2-amine;
3-(2-(6-tert-butylpyrimidin-4-yl)ethyl)-6-(3-methylpyridin-2-yl)quinolin-2-amine;
3-(2-(1H-indol-2-yl)ethyl)-6-o-tolylquinolin-2-amine;
3-(2-(5-isobutylpyridin-3-yl)ethyl)-6-o-tolylquinolin-2-amine;
3-(2-(1-benzyl-1H-pyrazol-4-yl)ethyl)-6-o-tolylquinolin-2-aminel;
6-(3-methylpyridin-2-yl)-3-(2-(6-(tetrahydro-2H-pyran-4-yl)pyrimidin-4-yl)ethyl)quinolin-2-amine;
3-(2-(5-neopentylpyridin-3-yl)ethyl)-6-o-tolylquinolin-2-amine;
3-(2-(5-(3,3-dimethylbutyl)pyridin-3-yl)ethyl)-6-o-tolylquinolin-2-amine;
6-o-tolyl-3-(3-(trifluoromethyl)phenethyl)quinolin-2-amine;
3-(2-(1-cyclohexyl-1H-pyrazol-4-yl)vinyl)-6-o-tolylquinolin-2-amine;
3-(2-(1-cyclohexyl-1H-pyrazol-4-yl)ethyl)-6-o-tolylquinolin-2-amine;
3-(2-(5-(tetrahydro-2H-pyran-2-yl)pyridin-3-yl)propyl)-6-o-tolylquinolin-2-amine;
3-(2-(5-cyclohexylpyridin-3-yl)propyl)-6-o-tolylquinolin-2-amine;
3-(2-(oxazol-5-yl)ethyl)-6-o-tolylquinolin-2-amine;
3-(2-(pyridin-2-yl)ethyl)-6-o-tolylquinolin-2-amine;
3-(2-(5-cyclopentylpyridin-3-yl)propyl)-6-o-tolylquinolin-2-amine;
3-(2-(5-(tetrahydro-2H-pyran-2-yl)pyridin-3-yl)ethyl)-6-o-tolylquinolin-2-amine;
(±)-(2-(2-amino-3-(2-(pyrimidin-5-yl)ethyl)quinolin-6-yl)-3-methylphenyl)(2-methylpyrrolidin-1-yl)methanone;
(2-(2-amino-3-(2-(pyrimidin-5-yl)ethyl)quinolin-6-yl)-3-methylphenyl)(pyrrolidin-1-yl)methanone; and
(2-(2-amino-3-((6-(trifluoromethyl)pyrimidin-4-yloxy)methyl)quinolin-6-yl)-3-methylphenyl)(pyrrolidin-1-yl)methanone.

10. A pharmaceutical composition comprising a compound according to any of claim 1-9 and a pharmaceutically acceptable excipient.

11. A process for preparing a compound according to any of claims 1-9, the process comprising the step of (a) reacting a compound 17

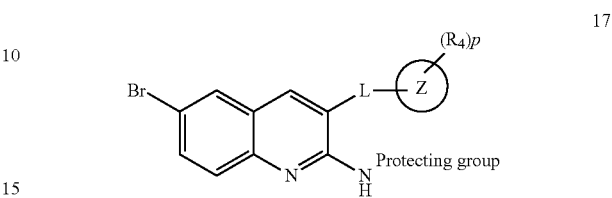

wherein L, Z, $R^4$ and p of Formula I are as defined herein, with a compound having the structure

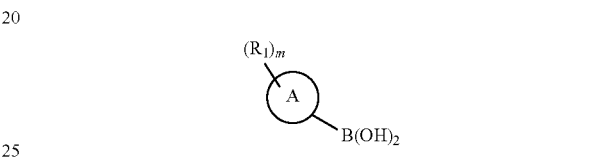

wherein ring A, $R^1$ and m are as defined herein to make a compound 18 of the formula

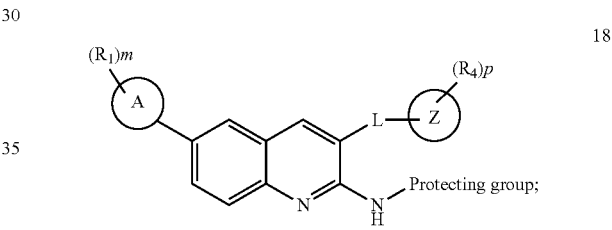

and
(b) deprotecting compound 18 to make a compound 19 of formula I

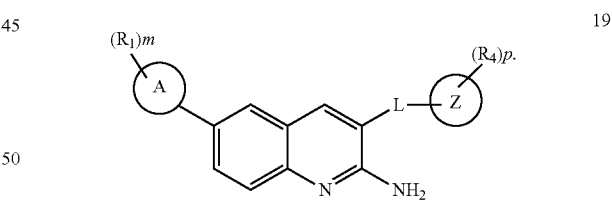

* * * * *